(12) United States Patent
Jurkiewicz

(10) Patent No.: US 11,026,031 B2
(45) Date of Patent: Jun. 1, 2021

(54) MAGNET POSITIONING IN AN EXTERNAL DEVICE

(71) Applicant: Tadeusz Jurkiewicz, Macquarie University (AU)

(72) Inventor: Tadeusz Jurkiewicz, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 16/806,512

(22) Filed: Mar. 2, 2020

(65) Prior Publication Data

US 2020/0204935 A1 Jun. 25, 2020

Related U.S. Application Data

(63) Continuation of application No. 16/129,740, filed on Sep. 12, 2018, now Pat. No. 10,582,318, which is a continuation of application No. 15/166,628, filed on May 27, 2016, now Pat. No. 10,104,482.

(51) Int. Cl.
*H04R 25/00* (2006.01)
*A61F 2/18* (2006.01)

(52) U.S. Cl.
CPC ............. *H04R 25/604* (2013.01); *A61F 2/18* (2013.01); *H04R 25/554* (2013.01); *H04R 25/65* (2013.01); *H04R 25/453* (2013.01); *H04R 25/456* (2013.01); *H04R 25/602* (2013.01); *H04R 2225/61* (2013.01); *H04R 2225/67* (2013.01); *H04R 2460/13* (2013.01)

(58) Field of Classification Search
CPC .......... H04R 25/606556; H04R 25/604; H04R 25/405; H04R 2460/13; H04R 2225/67; H04R 2225/023
See application file for complete search history.

(56) References Cited

U.S. PATENT DOCUMENTS

| | | | |
|---|---|---|---|
| 3,695,938 A | 10/1972 | Brodie | |
| 7,386,143 B2 | 6/2008 | Easter et al. | |
| 9,656,065 B2 * | 5/2017 | Tourrel | A61N 1/36038 |
| 2005/0070346 A1 | 3/2005 | Pan | |
| 2006/0030905 A1 | 2/2006 | Medina Malaver | |
| 2006/0183965 A1 | 8/2006 | Kasic, II et al. | |

(Continued)

FOREIGN PATENT DOCUMENTS

| | | |
|---|---|---|
| AU | 2009101370 A4 | 3/2013 |
| CN | 102245261 A | 11/2011 |

(Continued)

OTHER PUBLICATIONS

Office Action for CN Application No. 201780032758.5, dated May 26, 2020.

*Primary Examiner* — Sunita Joshi
(74) *Attorney, Agent, or Firm* — Pilloff Passino & Cosenza LLP; Martin J Cosenza

(57) ABSTRACT

A button sound processor, including an RF coil, such as an inductance coil, and a sound processing apparatus and a magnet, which can be a permanent magnet, wherein the button sound processor has a skin interface side configured to interface with skin of a recipient, and the button sound processor is configured such that the magnet is installable into the button sound processor from the skin interface side.

20 Claims, 33 Drawing Sheets

(56) References Cited

U.S. PATENT DOCUMENTS

| | | | |
|---|---|---|---|
| 2007/0053536 A1* | 3/2007 | Westerkull | H04R 25/606 |
| | | | 381/326 |
| 2008/0044049 A1 | 2/2008 | Ho et al. | |
| 2009/0030529 A1 | 1/2009 | Berrang et al. | |
| 2010/0179782 A1 | 7/2010 | Kimura et al. | |
| 2012/0029267 A1 | 2/2012 | Ball | |
| 2012/0214074 A1 | 8/2012 | Sato et al. | |
| 2012/0235636 A1 | 9/2012 | Partovi | |
| 2012/0302823 A1* | 11/2012 | Andersson | H04R 25/606 |
| | | | 600/25 |
| 2013/0004003 A1 | 1/2013 | Tada | |
| 2014/0121451 A1* | 5/2014 | Kasic | H04R 25/606 |
| | | | 600/25 |
| 2014/0364922 A1 | 12/2014 | Garnham et al. | |
| 2015/0038775 A1 | 2/2015 | Ruppersberg | |
| 2015/0087892 A1 | 3/2015 | Tourrel et al. | |
| 2015/0265842 A1 | 9/2015 | Ridler et al. | |
| 2015/0359553 A1 | 12/2015 | Harnisch | |
| 2015/0382114 A1* | 12/2015 | Andersson | H04R 25/606 |
| | | | 600/25 |
| 2016/0100260 A1 | 4/2016 | Ruppersberg et al. | |
| 2016/0381474 A1 | 12/2016 | Gustafsson et al. | |
| 2017/0078808 A1 | 3/2017 | Kennes | |
| 2017/0111728 A1 | 4/2017 | Kim et al. | |
| 2017/0347208 A1 | 11/2017 | Jurkiewicz | |

FOREIGN PATENT DOCUMENTS

| | | |
|---|---|---|
| CN | 103153393 A | 6/2013 |
| CN | 104511094 A | 4/2015 |
| JP | 2012191448 A | 10/2012 |
| KR | 101537380 B1 | 7/2015 |
| WO | 2015065442 A1 | 5/2015 |

\* cited by examiner

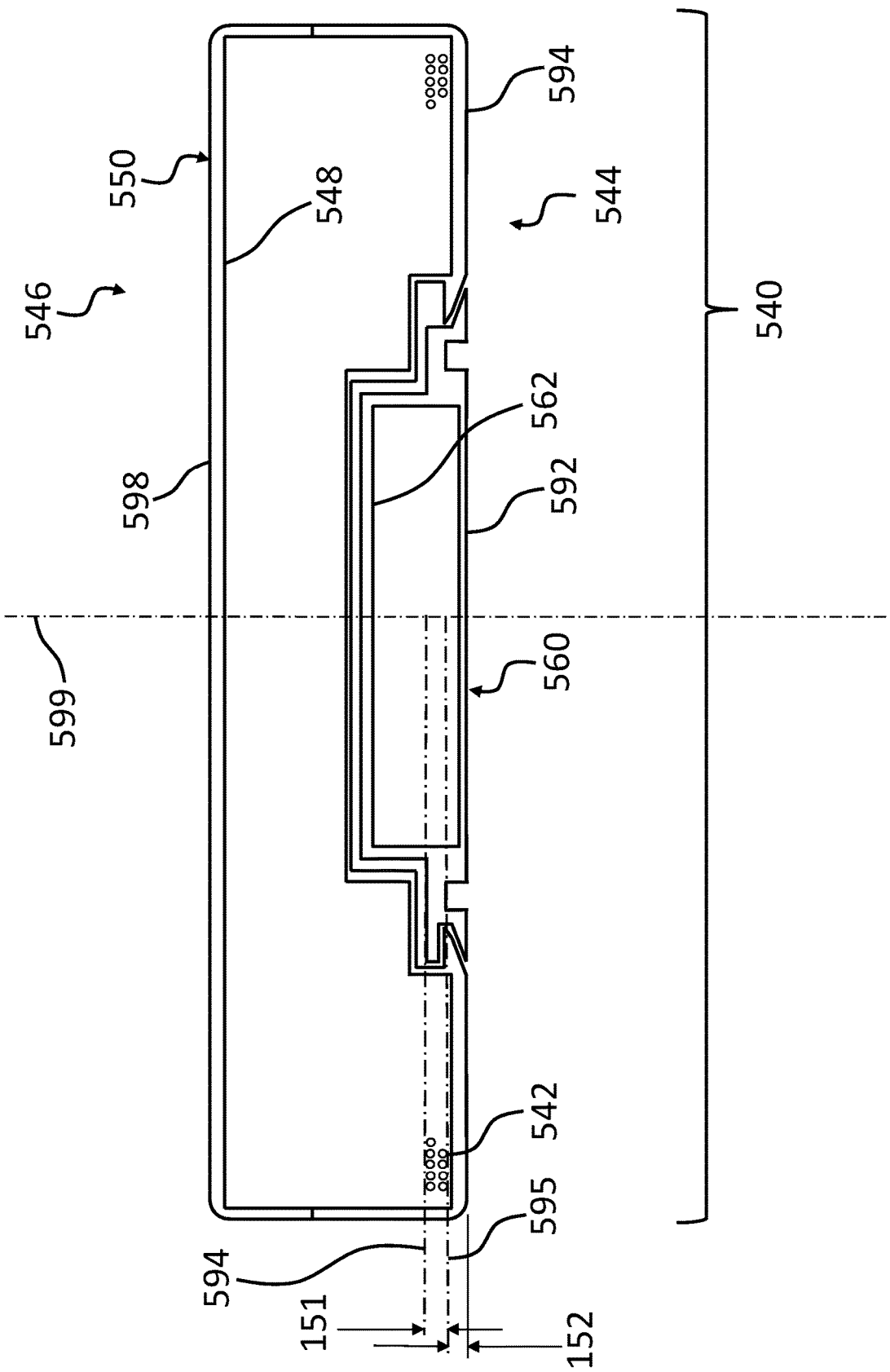

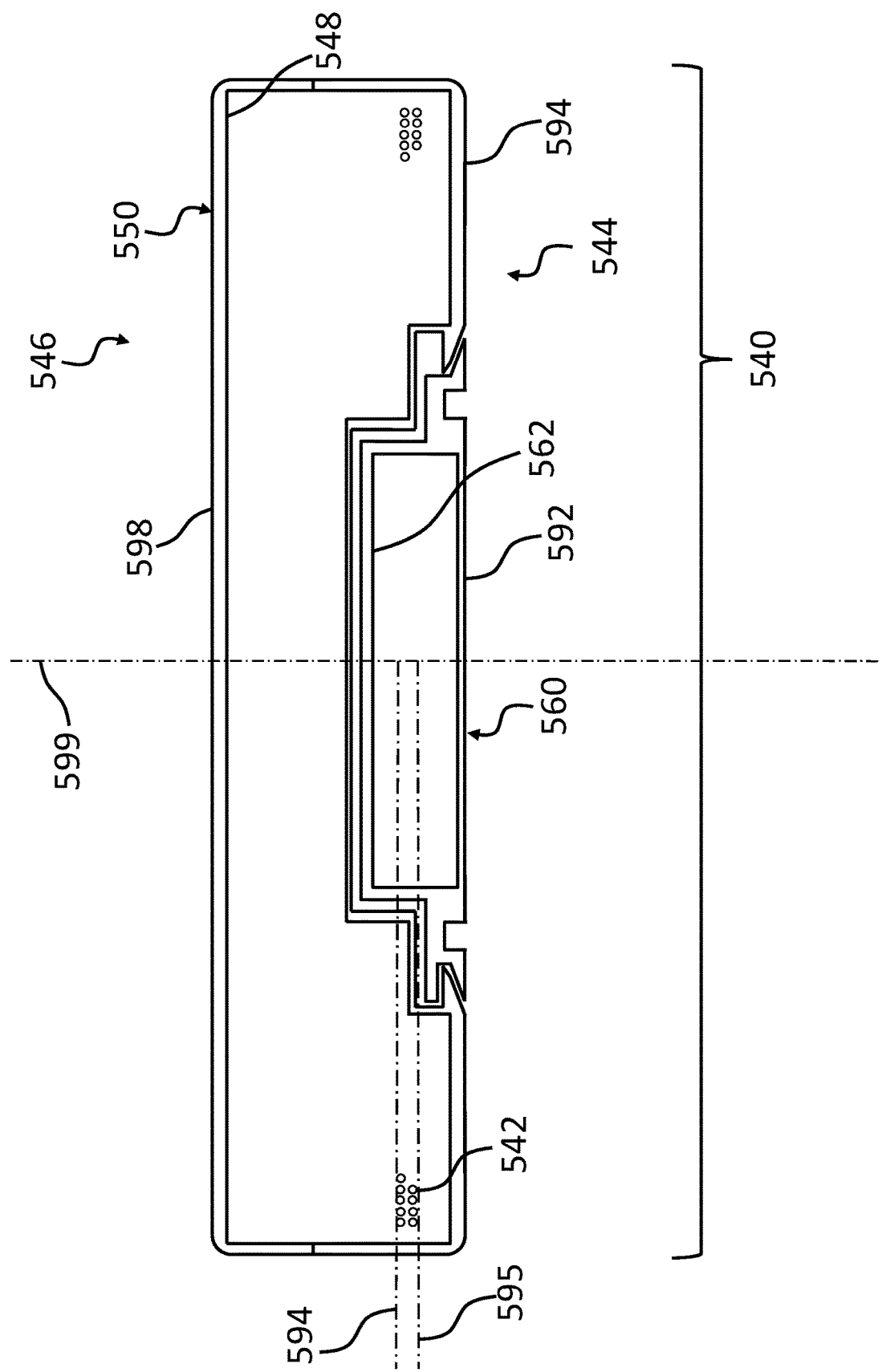

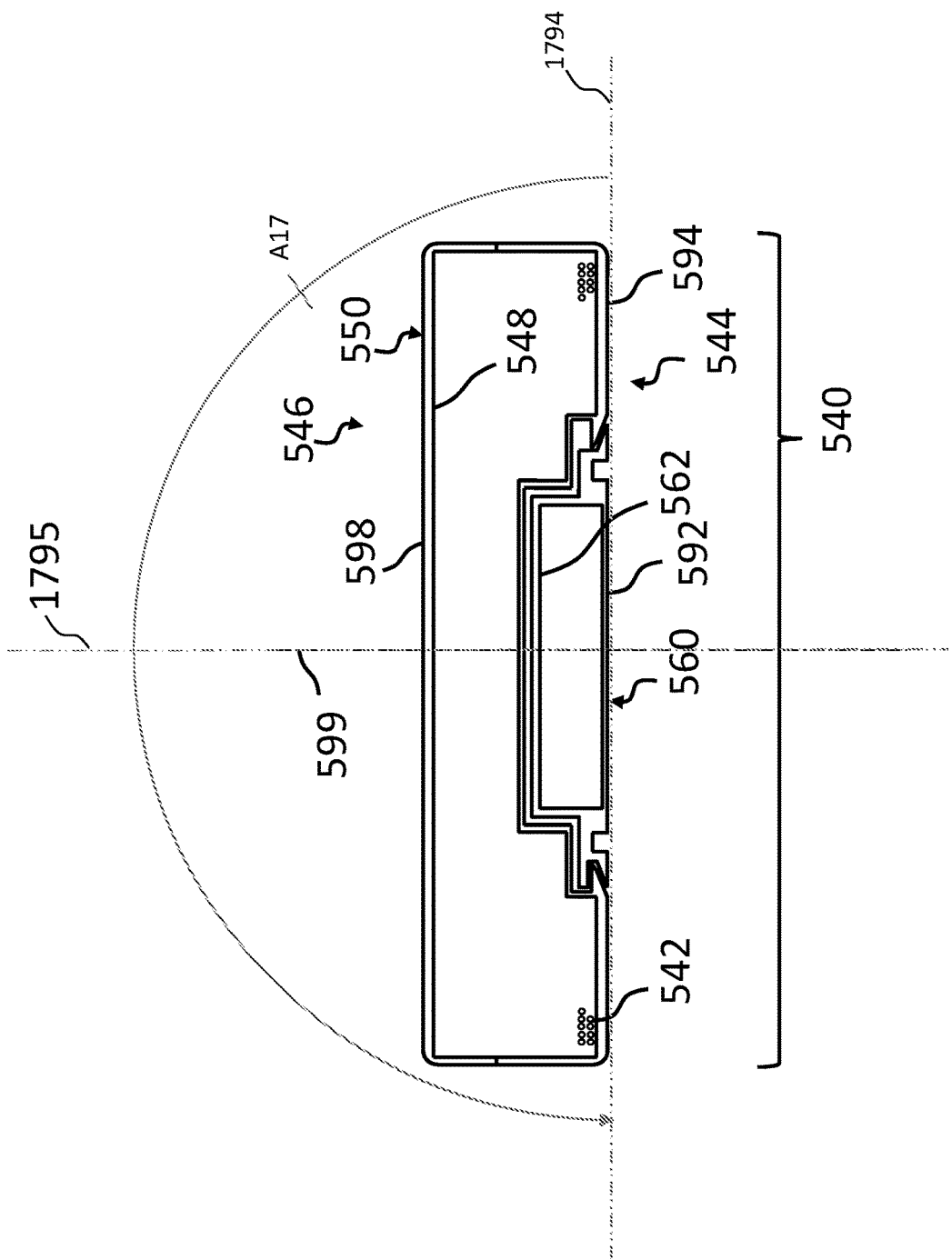

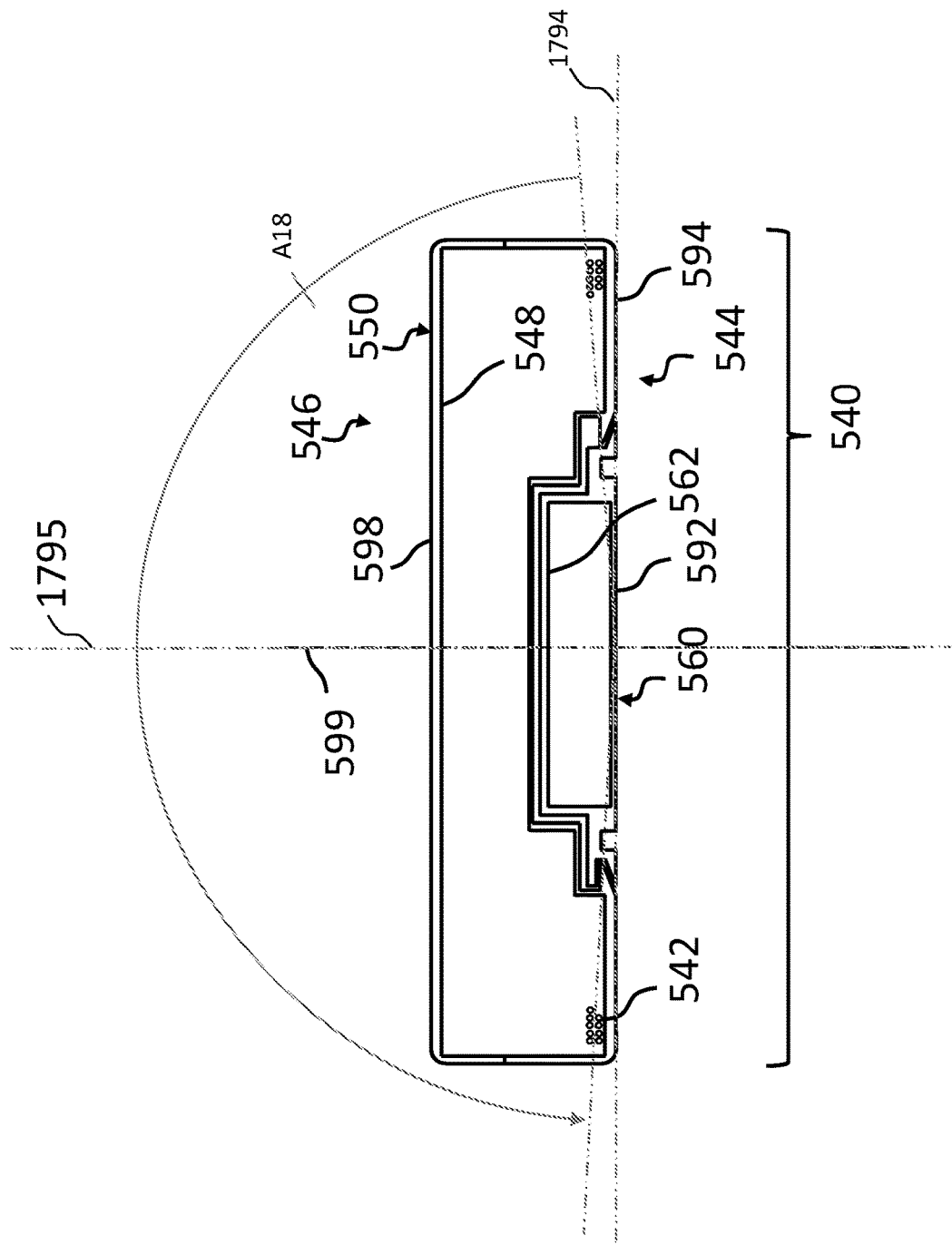

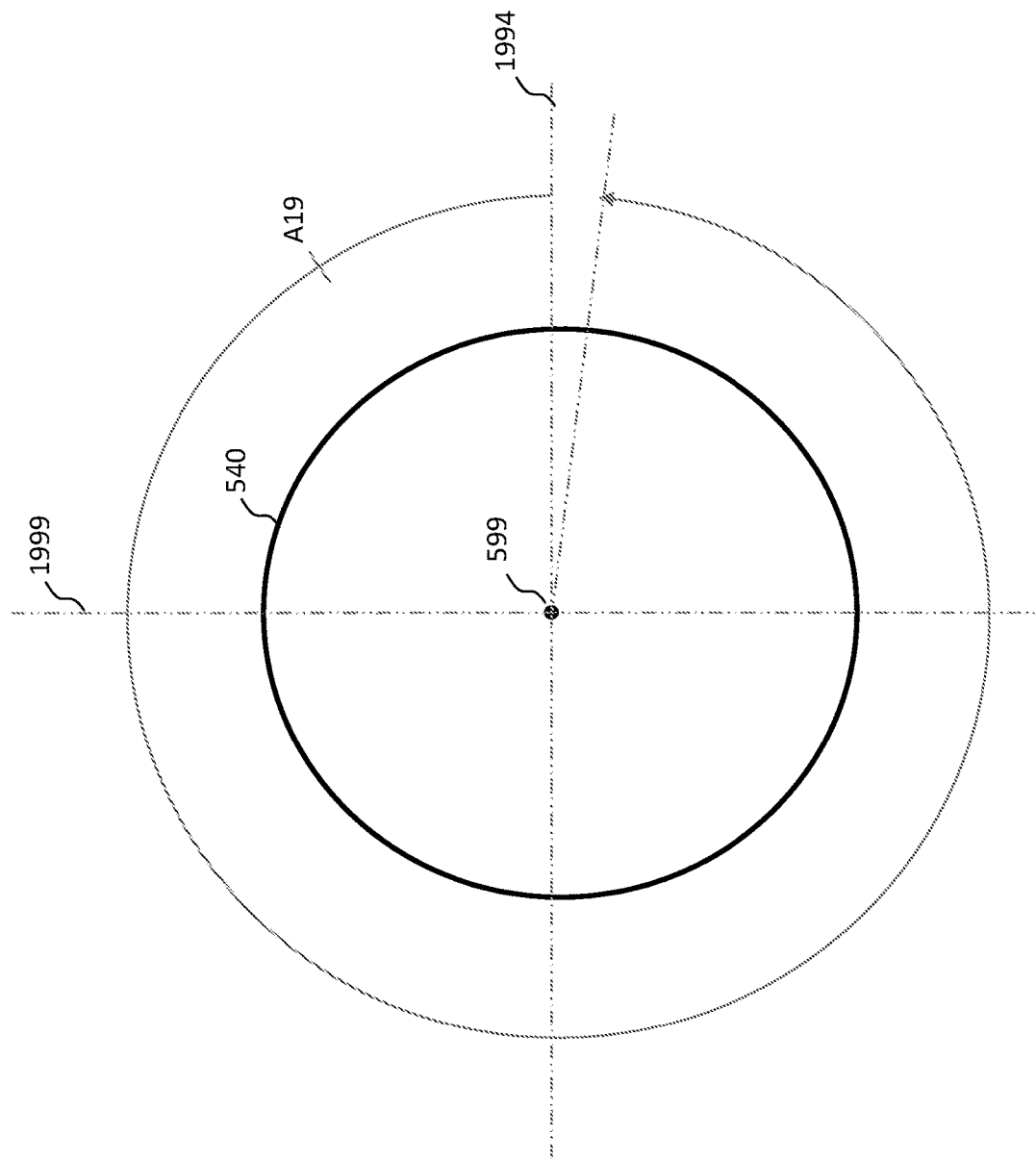

MAGNET POSITIONING IN AN EXTERNAL DEVICE

CROSS REFERENCE TO RELATED APPLICATIONS

This application is a Continuation application of U.S. patent application Ser. No. 16/129,740, filed Sep. 12, 2018, which is a Continuation application of U.S. patent application Ser. No. 15/166,628, filed May 27, 2016, the contents of all of these applications being incorporated herein by reference in their entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as bone conduction devices, convert a received sound into vibrations. The vibrations are transferred through the skull to the cochlea causing generation of nerve impulses, which result in the perception of the received sound. Bone conduction devices are suitable to treat a variety of types of hearing loss and may be suitable for individuals who cannot derive sufficient benefit from acoustic hearing aids, cochlear implants, etc., or for individuals who suffer from stuttering problems. Conversely, cochlear implants can have utilitarian value with respect to recipients where all of the inner hair inside the cochlea has been damaged or otherwise destroyed. Electrical impulses are provided to electrodes located inside the cochlea, which stimulate nerves of the recipient so as to evoke a hearing percept.

SUMMARY

In accordance with one aspect, there is a button sound processor, comprising an RF coil, sound processing apparatus, and a magnet, wherein the button sound processor has a skin interface side configured to interface with skin of a recipient, and the button sound processor is configured such that the magnet is installable into the button sound processor from the skin interface side.

In accordance with another aspect, there is a body piece configured for transcutaneous communication with a component implanted in a recipient, comprising an RF coil, and a magnet apparatus, wherein the RF coil is located on a first side of the body piece relative to an opposite side of the body piece, the body piece is configured such that the magnet apparatus is installable into the body piece from the first side, and the body piece is configured such that the magnet apparatus is rotationally lockable in place to the body piece.

In accordance with another aspect, there is a body piece configured for transcutaneous communication with an implanted component implanted in a recipient, comprising: a first housing, a magnet, a second housing, wherein the second housing completely envelops the magnet, the second housing forms an outer surface of the body piece, and at least one of the first housing completely covers the second housing with respect views of the body piece over 360 degrees of azimuthal angle and at least 170 continuous degrees of polar angle about of the first housing or the body piece is configured such that the second housing installable into the first housing at a skin interface side of the body piece.

In accordance with another aspect, there is a method, comprising obtaining a first portion of a headpiece for a prosthesis, the first portion including electronic components of the prosthesis, obtaining a second portion of the headpiece, the second portion including a first magnet, attaching the second portion to the first portion by inserting the second portion into a receptacle of the first portion from a side of the headpiece configured to interface with skin of the recipient.

BRIEF DESCRIPTION OF THE DRAWINGS

Some embodiments are described below with reference to the attached drawings, in which:

FIG. 15 is a schematic diagram of a cross-section of a portion of an exemplary external component according to an exemplary embodiment;

FIG. 16 is a schematic diagram of a cross-section of a portion of an exemplary external component according to an exemplary embodiment;

FIGS. 17, 18 and 19 present exemplary frame of reference is for some exemplary embodiments;

DETAILED DESCRIPTION

Figure 1:
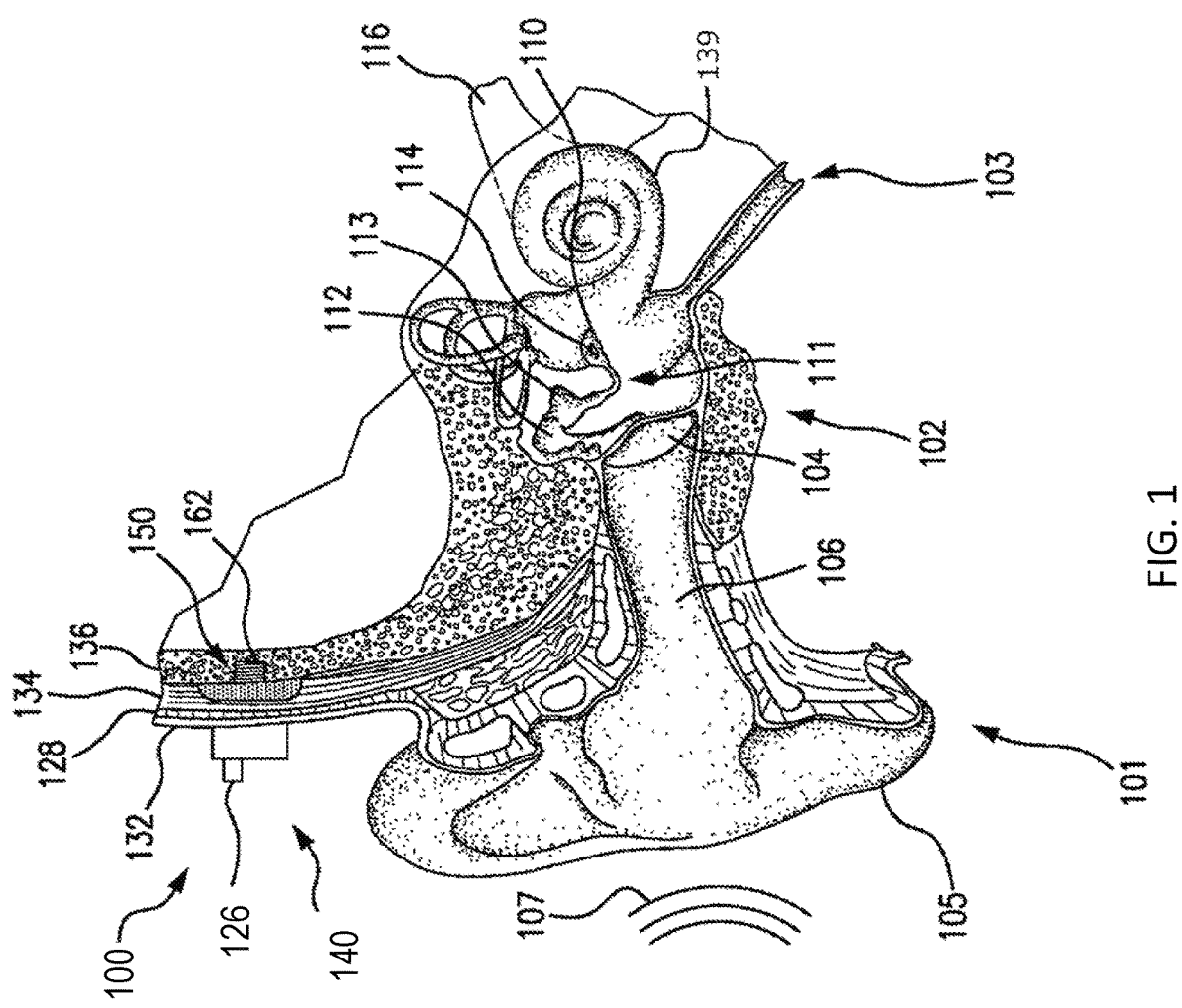
FIG. 1 is a perspective view of an exemplary bone conduction device in which at least some embodiments can be implemented.

Embodiments herein are described primarily in terms of a bone conduction device, such as an active transcutaneous bone conduction device. However, it is noted that the teachings detailed herein and/or variations thereof are also applicable to a cochlear implant and/or a middle ear implant. Accordingly, any disclosure herein of teachings utilized with an active transcutaneous bone conduction device also corresponds to a disclosure of utilizing those teachings with respect to a cochlear implant and utilizing those teachings with respect to a middle ear implant. Moreover, at least some exemplary embodiments of the teachings detailed herein are also applicable to a passive transcutaneous bone conduction device. It is further noted that the teachings detailed herein can be applicable to other types of prostheses, such as by way of example only and not by way of limitation, a retinal implant. Indeed, the teachings detailed herein can be applicable to any component that is held against the body that utilizes an RF coil and/or an inductance coil or any type of communicative coil to communicate with a component implanted in the body. That said, the teachings detailed herein will be directed by way of example only and not by way of limitation towards a component that is held against the head of a recipient for purposes of the establishment of an external component of the hearing prosthesis. In view of this, FIG. 1 is a perspective view of a bone conduction device 100 in which embodiments may be implemented. As shown, the recipient has an outer ear 101, a middle ear 102 and an inner ear 103. Elements of outer ear 101, middle ear 102 and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 210 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window 210 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. Bone conduction device 100 comprises an external component 140 and implantable component 150. As shown, bone conduction device 100 is positioned behind outer ear 101 of the recipient and comprises a sound input element 126 to receive sound signals. Sound input element 126 may comprise, for example, a microphone. In an exemplary embodiment, sound input element 126 may be located, for example, on or in bone conduction device 100, or on a cable extending from bone conduction device 100.

More particularly, sound input device 126 (e.g., a microphone) converts received sound signals into electrical signals. These electrical signals are processed by the sound processor. The sound processor generates control signals which cause the actuator to vibrate. In other words, the actuator converts the electrical signals into mechanical motion to impart vibrations to the recipient's skull.

Alternatively, sound input element 126 may be subcutaneously implanted in the recipient, or positioned in the recipient's ear. Sound input element 126 may also be a component that receives an electronic signal indicative of sound, such as, for example, from an external audio device. For example, sound input element 126 may receive a sound signal in the form of an electrical signal from an MP3 player electronically connected to sound input element 126.

Bone conduction device 100 comprises a sound processor (not shown), an actuator (also not shown), and/or various other operational components. In operation, the sound processor converts received sounds into electrical signals. These electrical signals are utilized by the sound processor to generate control signals that cause the actuator to vibrate.

In other words, the actuator converts the electrical signals into mechanical vibrations for delivery to the recipient's skull.

In accordance with some embodiments, a fixation system 162 may be used to secure implantable component 150 to skull 136. As described below, fixation system 162 may be a bone screw fixed to skull 136, and also attached to implantable component 150.

In one arrangement of FIG. 1, bone conduction device 100 can be a passive transcutaneous bone conduction device. That is, no active components, such as the actuator, are implanted beneath the recipient's skin 132. In such an arrangement, the active actuator is located in external component 140, and implantable component 150 includes a magnetic plate, as will be discussed in greater detail below. The magnetic plate of the implantable component 150 vibrates in response to vibration transmitted through the skin, mechanically and/or via a magnetic field, that is generated by an external magnetic plate.

In another arrangement of FIG. 1, bone conduction device 100 can be an active transcutaneous bone conduction device where at least one active component, such as the actuator, is implanted beneath the recipient's skin 132 and is thus part of the implantable component 150. As described below, in such an arrangement, external component 140 may comprise a sound processor and transmitter, while implantable component 150 may comprise a signal receiver and/or various other electronic circuits/devices.

Figure 2:
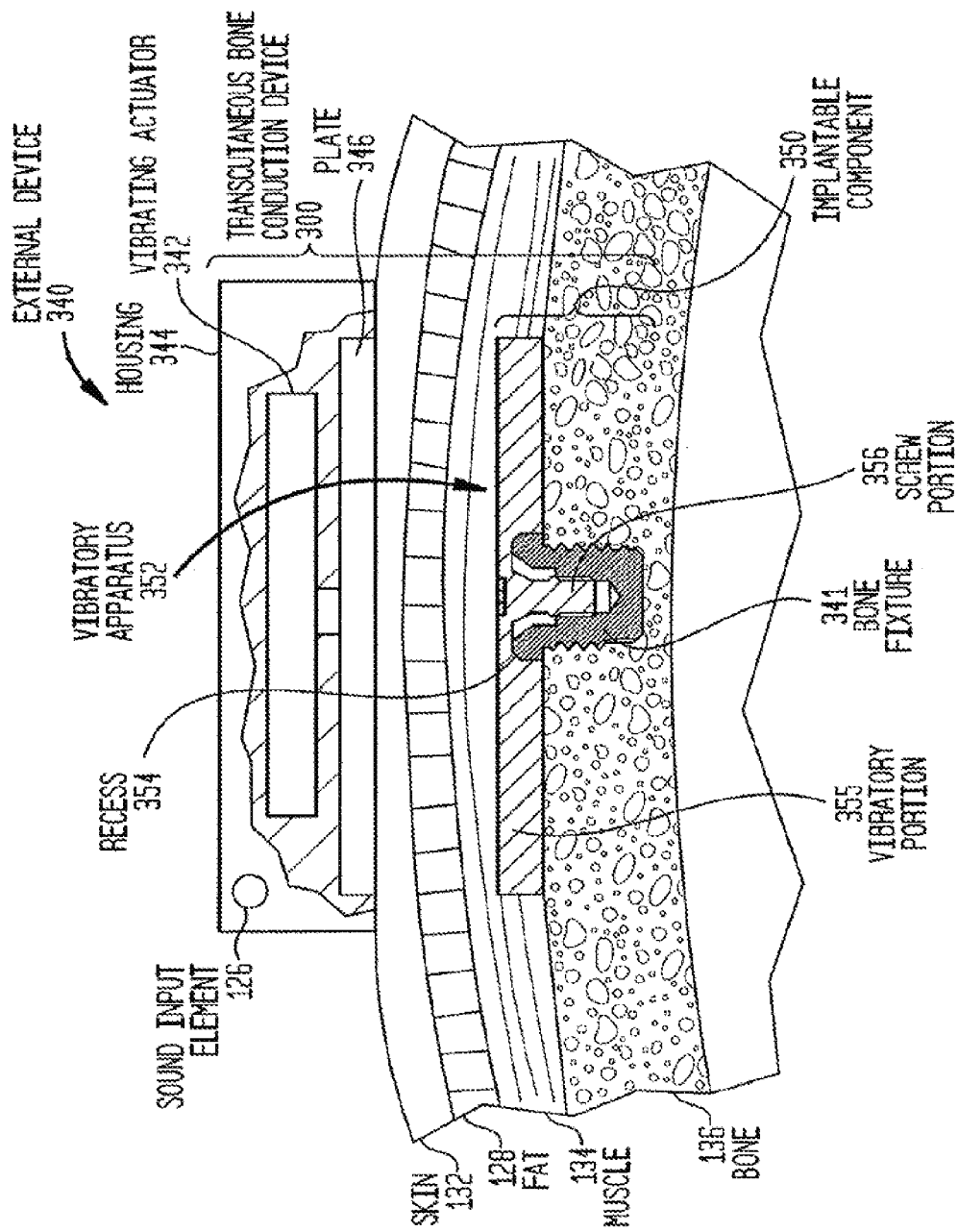
FIG. 2 is a schematic diagram conceptually illustrating a passive transcutaneous bone conduction device.
Figure 3:
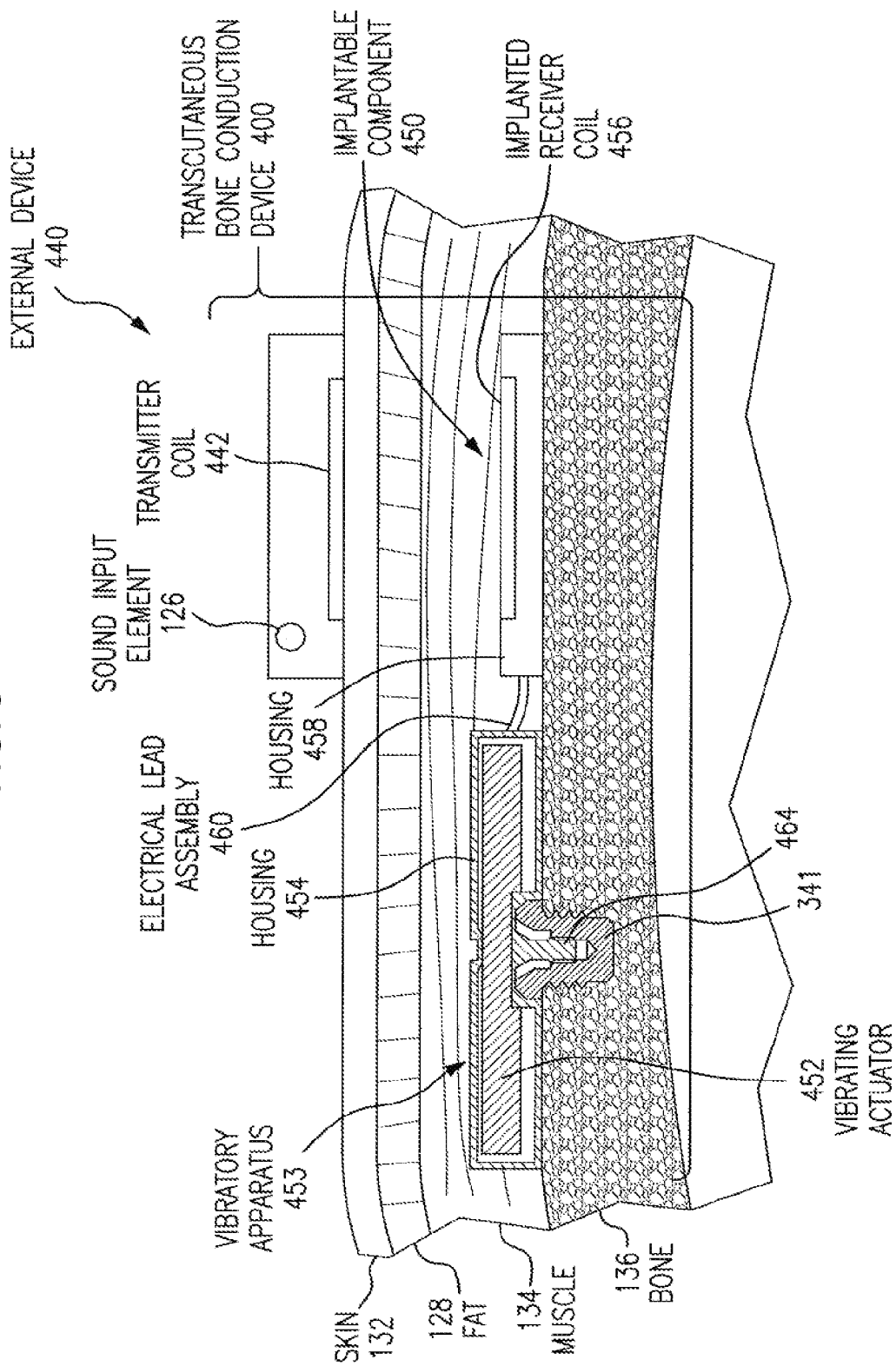
FIG. 3 is a schematic diagram conceptually illustrating an active transcutaneous bone conduction device in accordance with at least some exemplary embodiments.

FIG. 2 depicts an exemplary transcutaneous bone conduction device 300 that includes an external device 340 (corresponding to, for example, element 140 of FIG. 1) and an implantable component 350 (corresponding to, for example, element 150 of FIG. 1). The transcutaneous bone conduction device 300 of FIG. 3 is a passive transcutaneous bone conduction device in that a vibrating electromagnetic actuator 342 is located in the external device 340. Vibrating electromagnetic actuator 342 is located in housing 344 of the external component, and is coupled to plate 346. Plate 346 may be in the form of a permanent magnet and/or in another form that generates and/or is reactive to a magnetic field, or otherwise permits the establishment of magnetic attraction between the external device 340 and the implantable component 350 sufficient to hold the external device 340 against the skin of the recipient.

In an exemplary embodiment, the vibrating electromagnetic actuator 342 is a device that converts electrical signals into vibration. In operation, sound input element 126 converts sound into electrical signals. Specifically, the transcutaneous bone conduction device 300 provides these electrical signals to vibrating electromagnetic actuator 342, or to a sound processor (not shown) that processes the electrical signals, and then provides those processed signals to vibrating electromagnetic actuator 342. The vibrating electromagnetic actuator 342 converts the electrical signals (processed or unprocessed) into vibrations. Because vibrating electromagnetic actuator 342 is mechanically coupled to plate 346, the vibrations are transferred from the vibrating electromagnetic actuator 342 to plate 346. Implanted plate assembly 352 is part of the implantable component 350, and is made of a ferromagnetic material that may be in the form of a permanent magnet, that generates and/or is reactive to a magnetic field, or otherwise permits the establishment of a magnetic attraction between the external device 340 and the implantable component 350 sufficient to hold the external device 340 against the skin of the recipient. Accordingly, vibrations produced by the vibrating electromagnetic actuator 342 of the external device 340 are transferred from plate 346 across the skin to plate 355 of plate assembly 352. This can be accomplished as a result of mechanical conduction of the vibrations through the skin, resulting from the external device 340 being in direct contact with the skin and/or from the magnetic field between the two plates. These vibrations are transferred without penetrating the skin with a solid object, such as an abutment, with respect to a percutaneous bone conduction device.

As may be seen, the implanted plate assembly 352 is substantially rigidly attached to a bone fixture 341 in this embodiment. Plate screw 356 is used to secure plate assembly 352 to bone fixture 341. The portions of plate screw 356 that interface with the bone fixture 341 substantially correspond to an abutment screw discussed in some additional detail below, thus permitting plate screw 356 to readily fit into an existing bone fixture used in a percutaneous bone conduction device. In an exemplary embodiment, plate screw 356 is configured so that the same tools and procedures that are used to install and/or remove an abutment screw (described below) from bone fixture 341 can be used to install and/or remove plate screw 356 from the bone fixture 341 (and thus the plate assembly 352).

FIG. 3 depicts an exemplary embodiment of a transcutaneous bone conduction device 400 according to another embodiment that includes an external device 440 (corresponding to, for example, element 140B of FIG. 1) and an implantable component 450 (corresponding to, for example, element 150 of FIG. 1). The transcutaneous bone conduction device 400 of FIG. 3 is an active transcutaneous bone conduction device in that the vibrating electromagnetic actuator 452 is located in the implantable component 450. Specifically, a vibratory element in the form of vibrating electromagnetic actuator 452 is located in housing 454 of the implantable component 450. In an exemplary embodiment, much like the vibrating electromagnetic actuator 342 described above with respect to transcutaneous bone conduction device 300, the vibrating electromagnetic actuator 452 is a device that converts electrical signals into vibration.

External component 440 includes a sound input element 126 that converts sound into electrical signals. Specifically, the transcutaneous bone conduction device 400 provides these electrical signals to vibrating electromagnetic actuator 452, or to a sound processor (not shown) that processes the electrical signals, and then provides those processed signals to the implantable component 450 through the skin of the recipient via a magnetic inductance link. In this regard, a transmitter coil 442 of the external component 440 transmits these signals to implanted receiver coil 456 located in housing 458 of the implantable component 450. Components (not shown) in the housing 458, such as, for example, a signal generator or an implanted sound processor, then generate electrical signals to be delivered to vibrating electromagnetic actuator 452 via electrical lead assembly 460. The vibrating electromagnetic actuator 452 converts the electrical signals into vibrations.

The vibrating electromagnetic actuator 452 is mechanically coupled to the housing 454. Housing 454 and vibrating electromagnetic actuator 452 collectively form a vibratory apparatus 453. The housing 454 is substantially rigidly attached to bone fixture 341.

Figure 4:
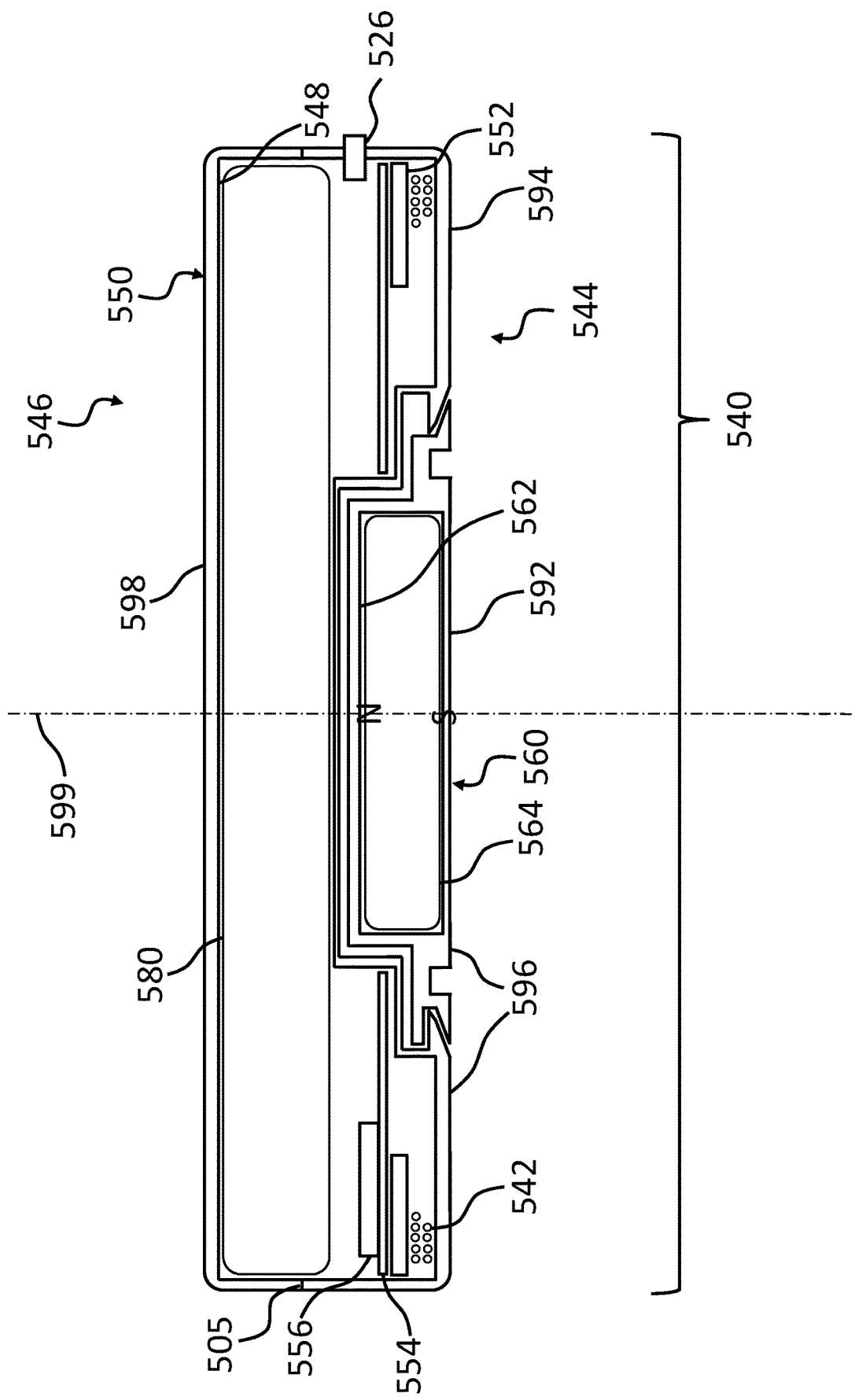
FIG. 4 is a schematic diagram of a cross-section of an exemplary external component according to an exemplary embodiment.

FIG. 4 depicts a cross-sectional view of an exemplary external component 540 corresponding to a device that can be used as external component 440 in the embodiment of FIG. 3. In an exemplary embodiment, external component 540 has all of the functionalities detailed above with respect to external component 440.

External component 540 comprises a first sub component 550 and a second sub component 560. It is briefly noted that back lines have been eliminated in some cases for purposes of ease of illustration (e.g., such as the line between sub component 550 and sub component 560—note that FIGS. 5 and 6 and 7 respectively depict these sub components in isolation relative to the other component). It is further noted that unless otherwise stated, the components of FIG. 4 are rotationally symmetric about axis 599, although in other embodiments, such is not necessarily the case.

In an exemplary embodiment, external component 540 is a so called button sound processor as detailed above. In this regard, in the exemplary embodiment of FIG. 4, the external component 540 includes a sound capture apparatus 526, which can correspond to the sound capture apparatuses 126 detailed above, and also includes a sound processor apparatus 556 which is in signal communication with or located on or otherwise integrated into a printed circuit board 554. Further as can be seen in FIG. 4, an electromagnetic radiation interference shield 554 is interposed between the coil 542 and the PCB 554 and/or the sound processor 556. In an exemplary embodiment, the shield 552 is a ferrite shield. These components are housed in or otherwise supported by subcomponent 550. Subcomponent 550 further houses or otherwise supports RF coil 542. Coil 542 can correspond to the coil 442 detailed above. In an exemplary embodiment, sound captured by the sound capture apparatus 526 is provided to the sound processor 556, which converts the sound into a processed signal which is provided to the RF coil 542. In an exemplary embodiment, the RF coil 542 is an inductance coil. The inductance coil is energized by the signal provided from the processor 556. The energized coil produces an electro-magnetic field that is received by an implanted coil in the implantable component 450, which is utilized by the implanted component 450 as a basis to evoke a hearing percept as detailed above.

The external component 540 further includes a magnet 564 which is housed in subcomponent 560. Subcomponent 560 is removably replaceable to/from subcomponent 550. In the exemplary embodiment of FIG. 4 when utilized in conjunction with the embodiment of FIG. 3, the magnet 564 forms a transcutaneous magnetic link with a ferromagnetic material implanted in the recipient (such as a magnet that is part of the implantable component 450, etc.). This transcutaneous magnetic link holds the external component 540 against the skin of the recipient. In this regard, the external component 550 includes a skin interface side 544, which skin interface side is configured to interface with skin of a recipient, and an opposite side 546 that is opposite the skin interface side 544. That is, when the external component 540 is held against the skin of the recipient via the magnetic link, such as when the external component 540 is held against the skin overlying the mastoid bone where the implantable component is located in or otherwise attached to the mastoid bone, side 546 is what a viewer who is looking at the recipient wearing the external component 540 can see (i.e., in a scenario where the external component 540 is held against the skin over the mastoid bone, and a viewer is looking at the side of the recipient's head, side 546 would be what the viewer sees of the external component 540).

Still with reference to FIG. 4, skin interface side 544 includes skin interface surfaces 592 and 594. Skin interface surface 592 corresponds to the bottom most surface of the sub component 560, and skin interface surface 594 corresponds to the bottom most surface of the subcomponent 550. Collectively, these surfaces establish surface assembly 596. Surface assembly 596 corresponds to the skin interface surfaces of the external component 540. It is briefly noted that in some exemplary embodiments, the arrangement of the external component 540 is such that the subcomponent 560 can be placed into the subcomponent 550 such that the bottom surface 592 is recessed relative to the bottom surface 594, and thus the surface 592 may not necessarily contract or otherwise interface with the recipient. It is further briefly noted that in some alternate exemplary embodiments, the arrangement of the external component 540 is reversed, where surface 594 does not contact the recipient because surface 592 remains proud of surface 594 after insertion of the subcomponent 560 into the subcomponent 550.

It is briefly noted that as used herein, the subcomponent 550 is utilized to shorthand for the external component 540. That is, external component 540 exists irrespective of whether the subcomponent 560 is located in the subcomponent 550 or otherwise attached to subcomponent 550.

In the embodiment of FIG. 4, the external component 550 is configured such that the subcomponent 560, and thus the magnet 564 and the housing containing magnet 564 (housing 562), is installable into the external component 540 (i.e., from subcomponent 550) from the skin interface side 544, and thus is installable into the housing 548 at the skin interface side. Also, in some embodiments, the subcomponent 560 is removable from the external component 550. This is represented functionally by arrows 597 and 598, where arrow 597 represents movements of the subcomponent(s) towards each other, thus corresponding to installation of the subcomponent 560, and thus the magnet 564, into the external component 540 and removal of the subcomponent 560 from the external component 540, and where arrow 598 represents a turning action of the subcomponent(s) relative to one another so as to "lock" subcomponent 562 subcomponent 550 as will be described in greater detail below, thus making the subcomponents rotationally lockable to one another. However, it is briefly noted that the turn locking as detailed herein does not correspond to mere thread engagement, such as by way of example how a bolt is threaded onto a nut, or visa-versa, because such does not result in locking of the components together. Some additional details of the arrangements utilized to obtain the aforementioned rotational locking are described in greater detail below. However, it is briefly noted that in some alternate embodiments, the subcomponents are snapped coupled or otherwise snapped locked to one another without rotation. By way of example only and not by way of limitation, the housing subcomponent containing the magnet can have detent receptacle located on a side surface, where a male detent of the housing containing the RF coil or the like interfaces with the receptacle so as to lock the subcomponents together. Any arrangement that can enable the retention of the subcomponents one another can utilize in at least some exemplary embodiments.

Still with reference to FIG. 4, it can be seen that the external component 540 includes a battery 580. In an exemplary embodiment, the battery 580 powers the sound processor 556 and/or the RF coil 542. As can be seen in FIG. 4, the battery 580 is positioned between the subcomponent 560, and thus the magnet 564, and the side 546 of the external component 540 opposite the side 544 configured to interface with the skin.

Figure 6:
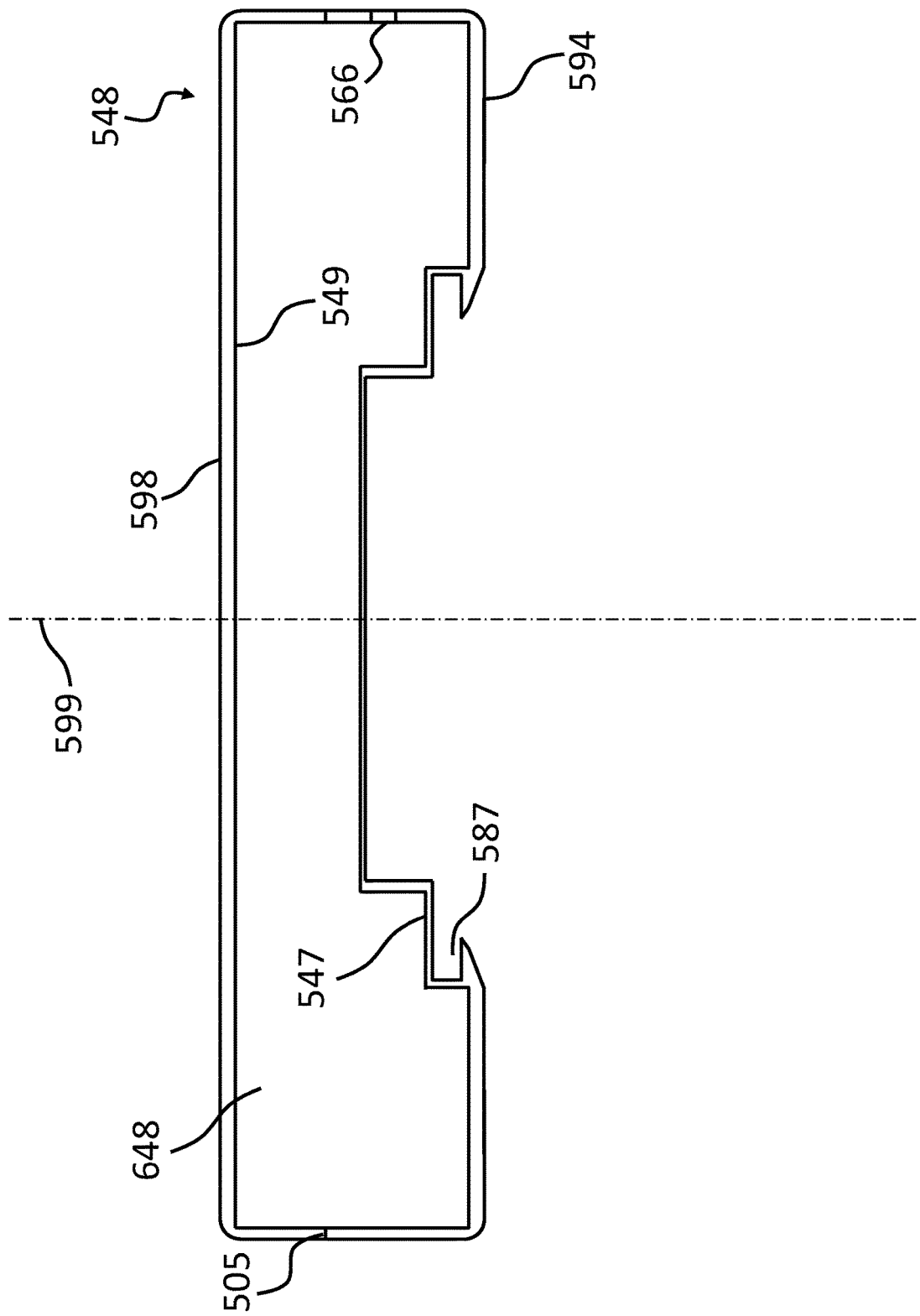
FIG. 6 is a schematic diagram of a cross-section of a portion of the embodiment of FIG. 4.

The subcomponent 550 comprises a housing 548 that contains the RF coil 542, the sound processor apparatus 556, and the battery 580. FIG. 6 depicts a cross-section of housing 548 without any other components therein. As can be seen, housing 548 includes hole 566 through which the sound capture apparatus 526 (not shown) extends. As can be understood from the figures, the housing 548 of the subcomponent 550 is such that subcomponent 560, and thus magnet 564, is completely external to the housing 548 of the subcomponent 550. (It is noted that in some embodiments, hole 556 is not present, and a microphone or other sound capture apparatus is located outside the housing 548 and is in wireless signal communication with the sound processor therein.)

In the embodiment depicted in FIG. 6, housing 548 includes housing subcomponent 547 and housing subcomponent 549. These two components are joined together at seam 505. It is briefly noted that while the embodiment presented in FIG. 6 presents to subcomponents of the housing 548, in an alternate embodiment, additional components are utilized to establish the housing, as will be described in greater detail below. In an exemplary embodiment, the subcomponent 547 and the subcomponent 549 are completely made out of a plastic material or other polymer material. That said, in an alternate embodiment, at least a portion of the subcomponents can be made out of a metal, such as by way of example, titanium. In an exemplary embodiment, the housing 548 is such that the housing, when assembled, provides sufficient structural integrity so as to protect the internal components from impact by another component (e.g., a soccer ball, the back of someone's hand, etc.). Some additional details of the functional features of the housing 548 will be described below.

Figure 7:
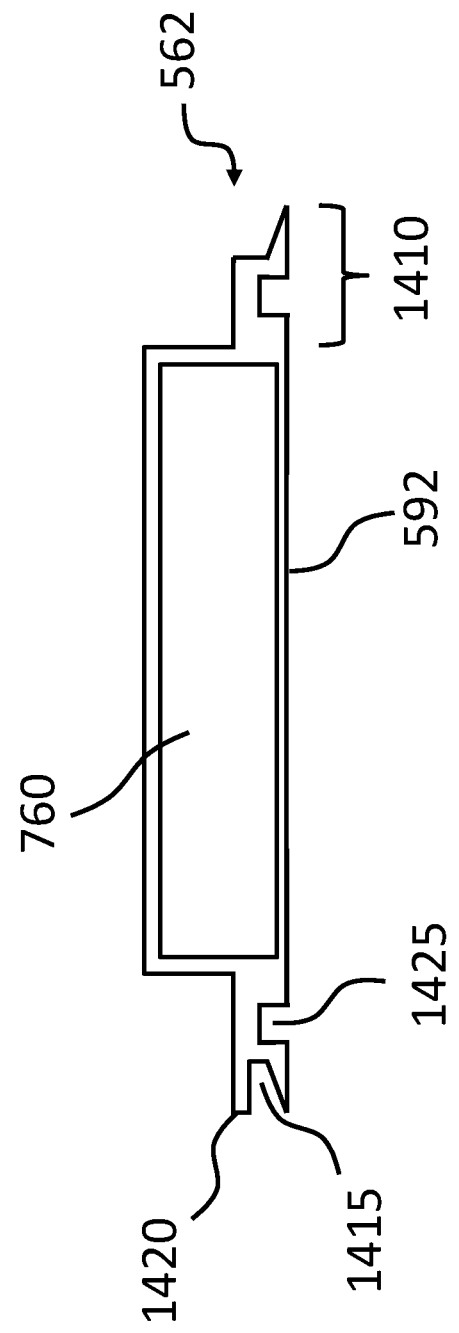
FIG. 7 is a schematic diagram of a cross-section of another portion of the embodiment of FIG. 4.

Still further, FIG. 7 depicts a cross-section of an exemplary subcomponent 560 that contains the magnet 564 (not shown). Subcomponent 560 also includes a housing 562. In this embodiment, housing 562 can be formed or otherwise casted about the magnet 564. Thus, in an exemplary embodiment, housing 562 can be a one piece housing/monolithic housing. That said, in an alternate embodiment, housing 562 can comprise two or more subcomponents that when joined together, form housing 562 so as to encapsulate or otherwise contain magnet 564.

Figure 8:
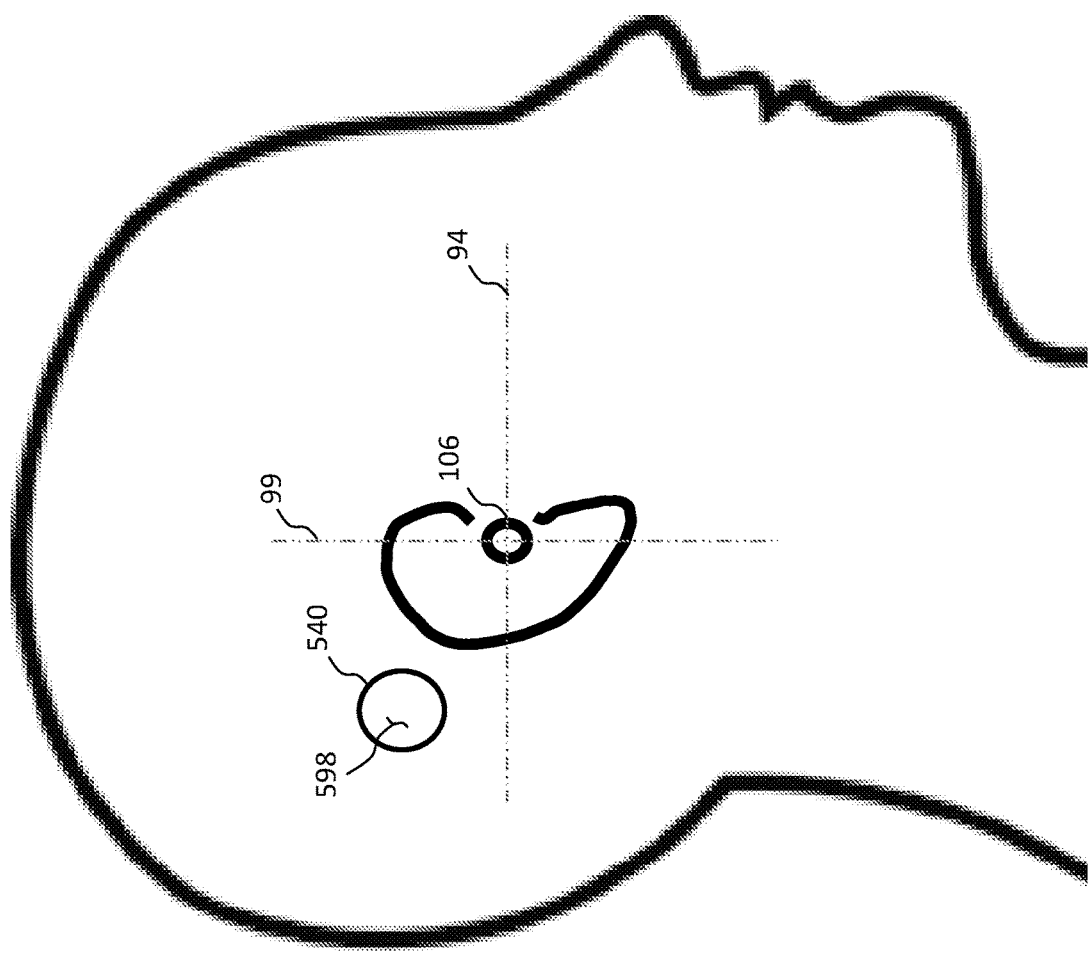
FIG. 8 is a schematic diagram of an exemplary placement of an external component according to an exemplary embodiment relative to the head of a human.

Briefly, FIG. 8 depicts an exemplary placement of the external component 540 against the head of a recipient from the frame of reference of the viewer looking at a right side of a recipient, where the recipient is looking ahead (the "right side" being the recipient's right side—the side of the recipient's right hand. Shown in FIG. 8 for purposes of reference is the pinna of the recipient, and the ear canal of the recipient 106. Horizontal axis 94 and vertical axis 99 are centered at the center of the outer opening of the ear canal 106. Horizontal axis 94 corresponds to the gravitational horizon, and vertical axis 99 is parallel to the direction of gravity.

As can be seen, surface 598 of the external component 540 is visible by the viewer. Conversely, the subcomponent 560 housing the magnet 564, corresponding to a magnet housing apparatus in an exemplary embodiment, is only visible from the skin interface side 544. The magnet housing apparatus is not visible from the opposite side 546 from the skin interface side 544 (the side visible in FIG. 8).

Figure 9:
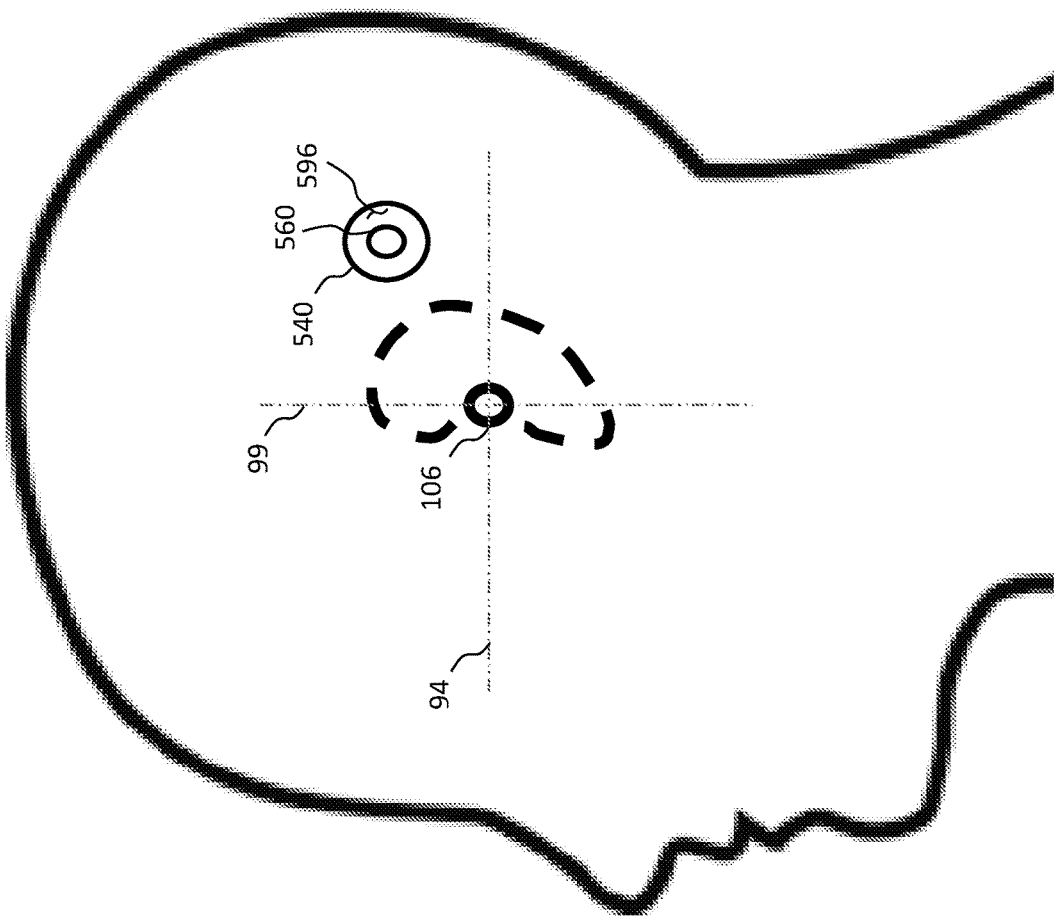
FIG. 9 is a schematic diagram depicting the placement of the external component placed according to FIG. 8, except with respect to another frame of reference.

Corollary to the above, FIG. 9 depicts the exemplary placement of FIG. 8 except when looking from the inside of the recipient (i.e., at the location of the brain) out. As can be seen, the subcomponent 560 (the magnet housing apparatus) is now visible, along with surface assembly 596. (This illustration is presented under the fictitious scenario where the skin supporting the external component 540 is transparent.) Thus, it can be understood that at least some exemplary embodiments detailed herein are such that the subcomponent 560 is only visible from the skin interface side 544 of the external component 540.

Figure 10:
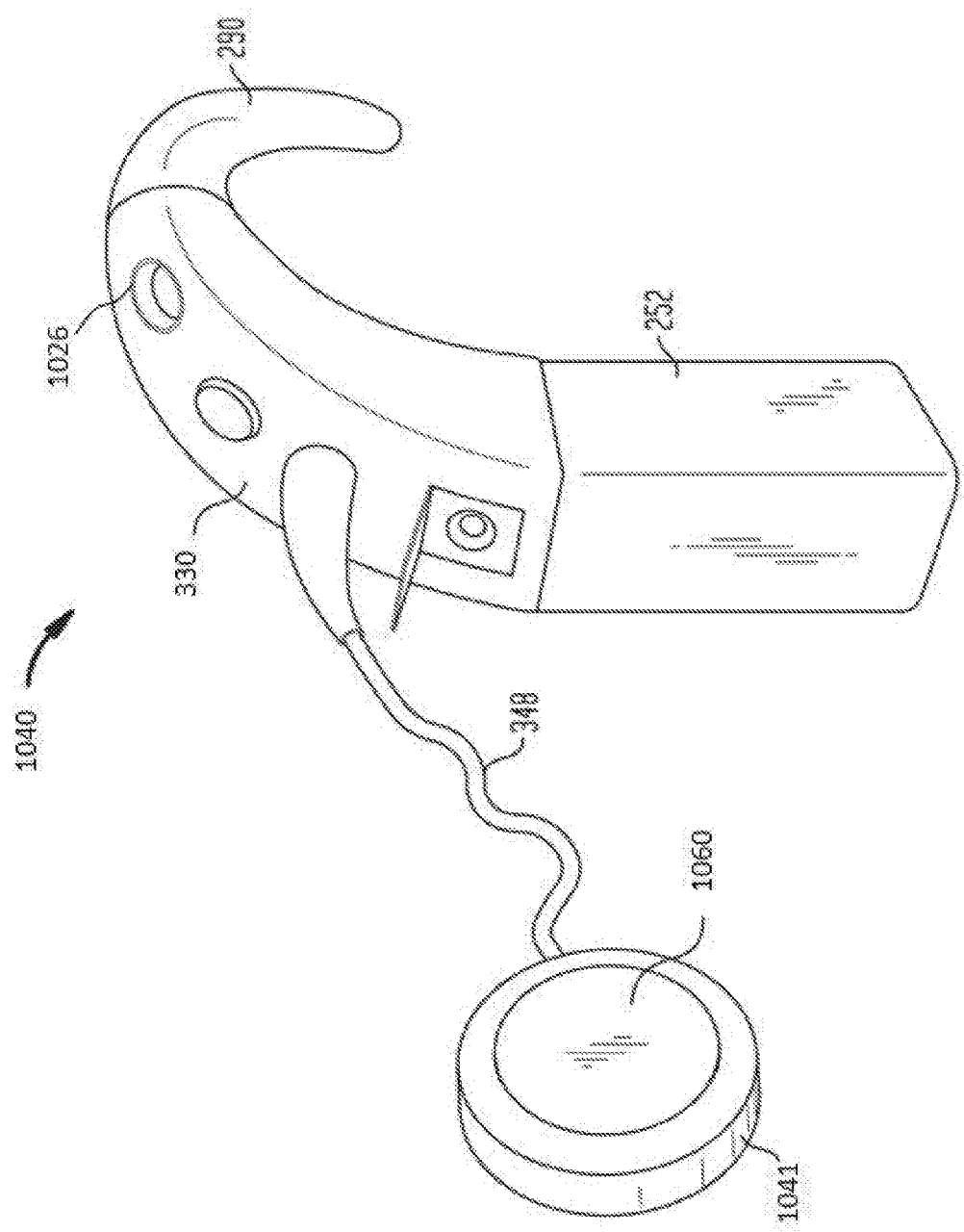
FIG. 10 is a schematic diagram depicting another exemplary embodiment of an external component.

FIG. 10 depicts an alternate embodiment of an external component of a bone conduction device, BTE device 1040, which can be used in place of external component 440 detailed above, and otherwise has the functionality thereof in at least some exemplary embodiments. More specifically, FIG. 10 depicts a perspective view of a BTE device of a hearing prosthesis. BTE device 1040 includes one or more microphones 1026, and may further include an audio signal under a cover 220 on the spine 330 of BTE device 1040. It is noted that in some other embodiments, one or both of these components (microphone 1026 and/or the jack) may be located on other positions of the BTE device 1040, such as, for example, the side of the spine 330 (as opposed to the back of the spine 330, as depicted in FIG. 10), the ear hook 290, etc. FIG. 10 further depicts battery 252 and ear hook 290 removably attached to spine 330.

In an exemplary embodiment, the external component 1040 includes a sound processor or the like located in spine 330. The sound processor is in electronic communication with headpiece 1041 via cable 348. Headpiece 1041 can include an RF coil such as those detailed above. Concomitant with the teachings detailed above with respect to the sound processor of various other embodiments detailed herein, sound captured by the microphone 1026 is transduced into an electrical signal that is supplied to the sound processor, either directly or indirectly. The sound processor processes the signal and converts it into a signal or otherwise processes the signal so as to output a signal via cable 348 to the RF coil located in headpiece 1041, where the RF coil functions according to the teachings detailed above, in at least some exemplary embodiments.

Headpiece 1041 includes a magnet apparatus 351. This magnet apparatus can have the functionality of the subcomponent 550 detailed above.

While the embodiment depicted in FIG. 10 utilizes a cable 348 to establish communication between the spine 330 and the headpiece 1041, in an alternative embodiment, a wireless link is utilized to communicate between the spine 330 and the headpiece 1041.

Figure 11:
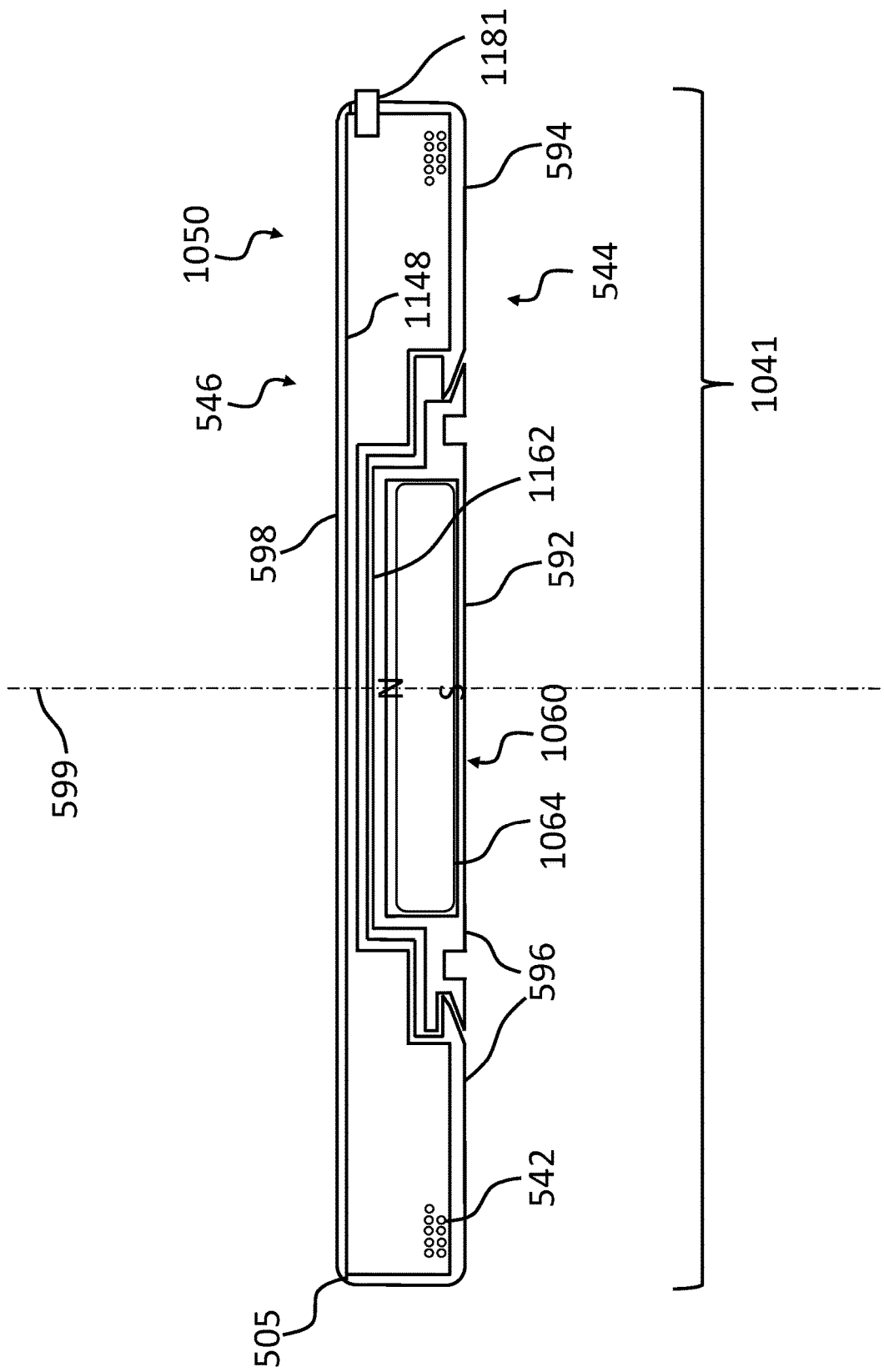
FIG. 11 is a schematic diagram of a cross-section of another exemplary external component according to an exemplary embodiment.

FIG. 11 depicts a cross-sectional view of the headpiece 1041. Here, FIG. 11 is presented with the same frame of reference with respect to FIG. 4 detailed above. Like reference numbers have been utilized in some instances for convenience of conveyance of concept. As can be seen, headpiece 1041 includes a subcomponent 1050 and a subcomponent 1060. In an exemplary embodiment, the subcomponent respectively corresponds, in a conceptual manner, to subcomponents 550 and 560 detailed above. In this regard, subcomponent 550 includes a housing 1148, which contains an RF coil 542. The housing 1148 comprises two sub housings that are joined together at seam 505. Subcomponent 1050 includes cable jack 1181, which is configured to connect the cable 348 to the headpiece 1041.

Sub component 1060 includes housing 1162 which contains magnet 1064. In an exemplary embodiment, the functionalities of the components depicted in FIG. 11 can correspond to the functionalities of similar components presented in FIG. 4. In this regard, some of these functionalities will be described in detail below. Briefly, it is noted that the embodiment of FIG. 11 is such that the housing 1148 has a height that is less than the housing 548 of the embodiment of FIG. 4. In the exemplary embodiment depicted in FIG. 11, there is no battery and no sound processor present in headpiece 1041 (because these components can be located in the spine 330, where headpiece 1041 is in signal communication with via cable jack 1181). Thus, the housing can be thinner. Corollary to this is that in this exemplary embodiment, the magnet 1064 can be thinner than magnet 564 detailed above because, in this exemplary embodiment, the mass of the headpiece 1041 is less than the mass of the external component 540 (which contains a magnet, a sound processor, etc.). Thus, the strength of the magnet that is utilized to hold the external component (or pertinent portions thereof) against the skin of the recipient can be less for the embodiment of FIG. 11 relative to that of the embodiment of FIG. 4 to achieve the same result, all other things being equal.

In the embodiment of FIG. 11, the subcomponents interface with one another and are removable and/or attachable with respect to one another in a manner that is the same as or otherwise similar to the embodiment of FIG. 4, where again, additional details of such will be provided below.

In view of the embodiment of FIG. 11, it is to be understood that in an exemplary embodiment, there is a body piece, such as, for example, head piece 1041 (it is noted that in some alternate embodiments, the teachings detailed herein and/or variations thereof can be applicable to components that are not headpieces, but instead, or torso pieces and/or limb pieces etc.) configured for transcutaneous communication with a component implanted in a recipient (e.g., implantable component 450 of FIG. 4). In view of FIG. 11, it can be seen that the body piece includes an RF coil 542 and a magnet apparatus in the form of a subcomponent 1060. As can be seen, the RF coil is located on a first side of the body piece relative to an opposite side of the body piece. In this regard, with respect to a plane normal to longitudinal axis 599 bifurcating the geometric body established by the headpiece 1041 (a plane through the geometric center of the headpiece 1041), the RF coil 542 would be located entirely and/or a majority of the RF coil 542 would be located on one side of that plane. Here, the sides of the body piece can be side 544 and 546, the side being opposite to one another. It is further noted that in an exemplary embodiment, with respect to a plane normal to the longitudinal axis 599 bifurcating the center of mass established by the subcomponent 1050 (i.e., without subcomponent 1040 which, owing to the weight of the magnet 1064 would bias the center of mass to one side versus the other a disproportionate amount), the RF coil 542 would be located entirely and/or a majority of the RF coil 542 would be located on one side of the plane. That said, in an alternate embodiment, with respect to a plane normal to the longitudinal axis 599 bifurcating the center of mass established by the entire headpiece 1041 (and also, with respect to the embodiment of FIG. 4 (where external component 550 also corresponds to a body piece), a plane bifurcating center of mass established by the entire external component 540), the RF coil 542 would be located entirely and/or a majority of the RF coil 542 would be located on one side of this plane.

Consistent with the embodiments associated with FIG. 4 detailed above, the body piece of this exemplary embodiment is configured such that the magnet apparatus 1060 is installable into the body piece from the first side. Still further, in at least some exemplary embodiments, the body piece is configured such that the magnet apparatus 1060 is rotationally lockable in place to the body piece. Again, some additional details of the arrangement whereby the subcomponents are locked together to each other are described in greater detail below.

Consistent with the teachings associated with FIG. 4, the embodiment of FIG. 11 is such that the aforementioned first side is a skin interface side (side 544) that consists of a first structure and a second structure. Here, the first structure can correspond to the bottom subcomponent of the housing 1148 and/or 548 (e.g., with respect to the embodiment of FIG. 4, subcomponent 547, which establishes surface 594). Still further, the second structure can be established by the magnet apparatus 1060 (or 560), where the bottom of housing 1162 (corresponding to housing 562 of the magnet apparatus 560) of magnet apparatus 1060 establishes surface 592. In this exemplary embodiment, the first structure established by the housing 1148 houses or otherwise contains the RF coil 542, and the second structure established by housing 1162 houses or otherwise contains the magnet 1064.

With respect to the embodiments of FIG. 4 and FIG. 11, it can be seen that in these exemplary embodiments, the housing of the subcomponent 1050 that contains the RF coil presents a complete barrier between the magnet of the respective embodiment and a side of the body piece opposite the aforementioned first side (the skin facing side, side 544). For example, with respect to FIG. 8, when looking at the recipient from that perspective, where the recipient is wearing the body piece, a portion of the housing entirely covers the magnet apparatus. That is, there is no passage from the "outside" (the side where the viewer is positioned) to the magnet apparatus, not even a pinhole.

As noted above, in an exemplary embodiment, the housing components can be formed as monolithic components. In this regard, in an exemplary embodiment, housing subcomponent 549 can be a monolithic component that extends completely across surface 598, and in some embodiments, extends around surface 598 (e.g., down to seam 505 with respect to the embodiment of FIG. 4). Conversely, with respect to the skin interface side 544, while the respective surfaces 594 and 592 can be established by respective monolithic components (monolithic with respect to the surfaces—in an exemplary embodiment, housing 1162 can be made from two separate components that are snapped coupled together at the top, or elsewhere (e.g., lower), but if the bottom surface 592 is established by a monolithic sub housing component, the surface 592 is still established by a monolithic surface. Accordingly, in an exemplary embodiment, a first side of the body piece is established by two surfaces respectively established by monolithic structures with respect to those surfaces (e.g., surfaces 594 and 592) and the opposite side of the body piece from that first side is established entirely by one surface established by monolithic structure with respect to that surface.

Note further, that in an exemplary embodiment, the first side of the body piece (e.g., side 544) is established by two monolithic structures with respect to the first side. In this regard, these can be the monolithic structures of the housing subcomponent 547 and the housing 562. It is noted that this feature is achieved even though the housing 548 is not in and of itself a monolithic structure, at least not where the two housing components are snapped coupled to one another or the like. Still further, that in this exemplary embodiment, the side of the body piece opposite the first side is established entirely by a second monolithic structure with respect to that side. Here, this can correspond to the sub component 549 of the housing 562 detailed above.

Figure 12:
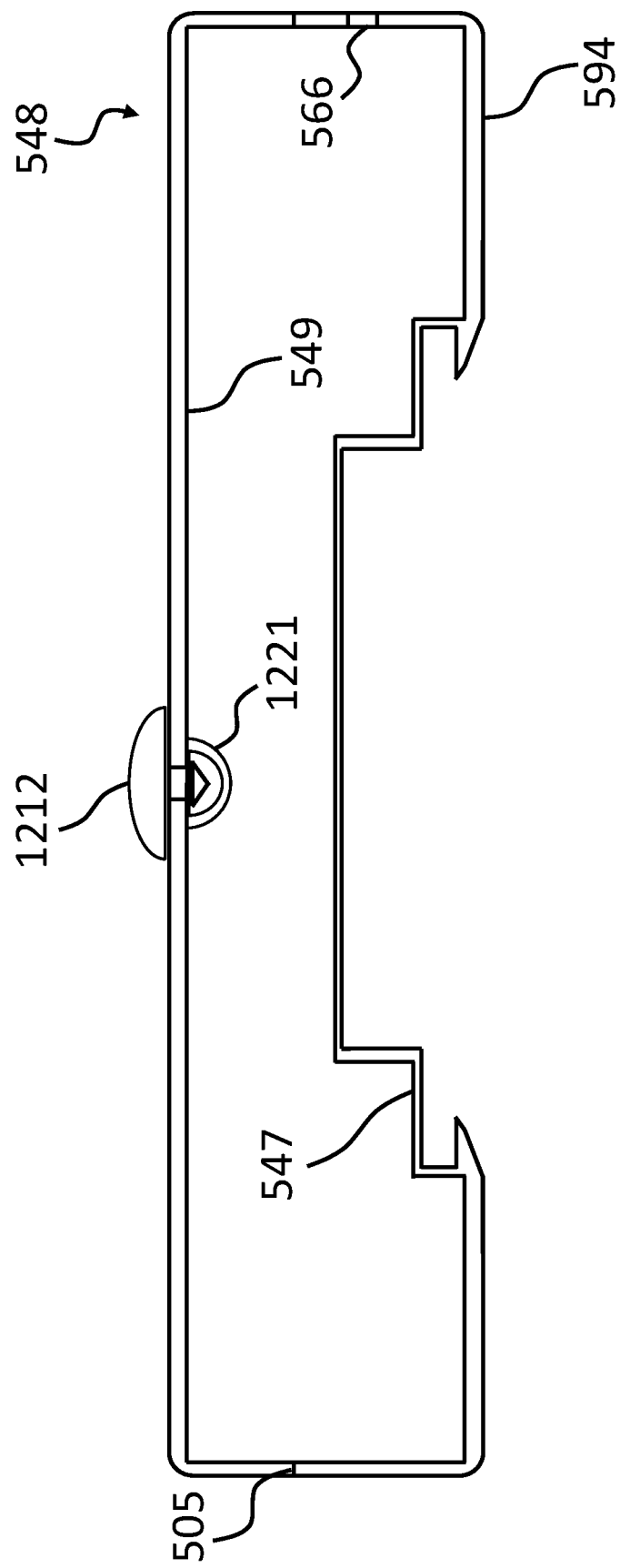
FIG. 12 is a schematic diagram of a cross-section of a portion of an exemplary external component according to an exemplary embodiment.

That said, some exemplary embodiments might include components that are located on surface 598 of housing 548. For example, an emblem can be snapped coupled or otherwise adhesively coupled to surface 598. Accordingly, in an exemplary embodiment, the side facing the viewer with respect to FIG. 8 of the body piece can include a monolithic structure that extends completely across the body piece from one side to the other that provides no passage from the outside to the inside of the housing with respect to that side (there could be a passage on the lateral sides, such as the passage corresponding to 566). Such can be achieved via the embodiment of FIG. 12, which depicts emblem 1212 snap coupled to housing 548, where housing subcomponent 549 includes a deviation 1221 in the housing wall thereof that provides space for the male portion of emblem 1212 that extends beyond the top of the housing 548 as seen, where deviation 1221 provides a barrier between the inside of the housing and the side of the housing 546 even though there is a hole through the top surface of the housing subcomponent 549.

Figure 13:
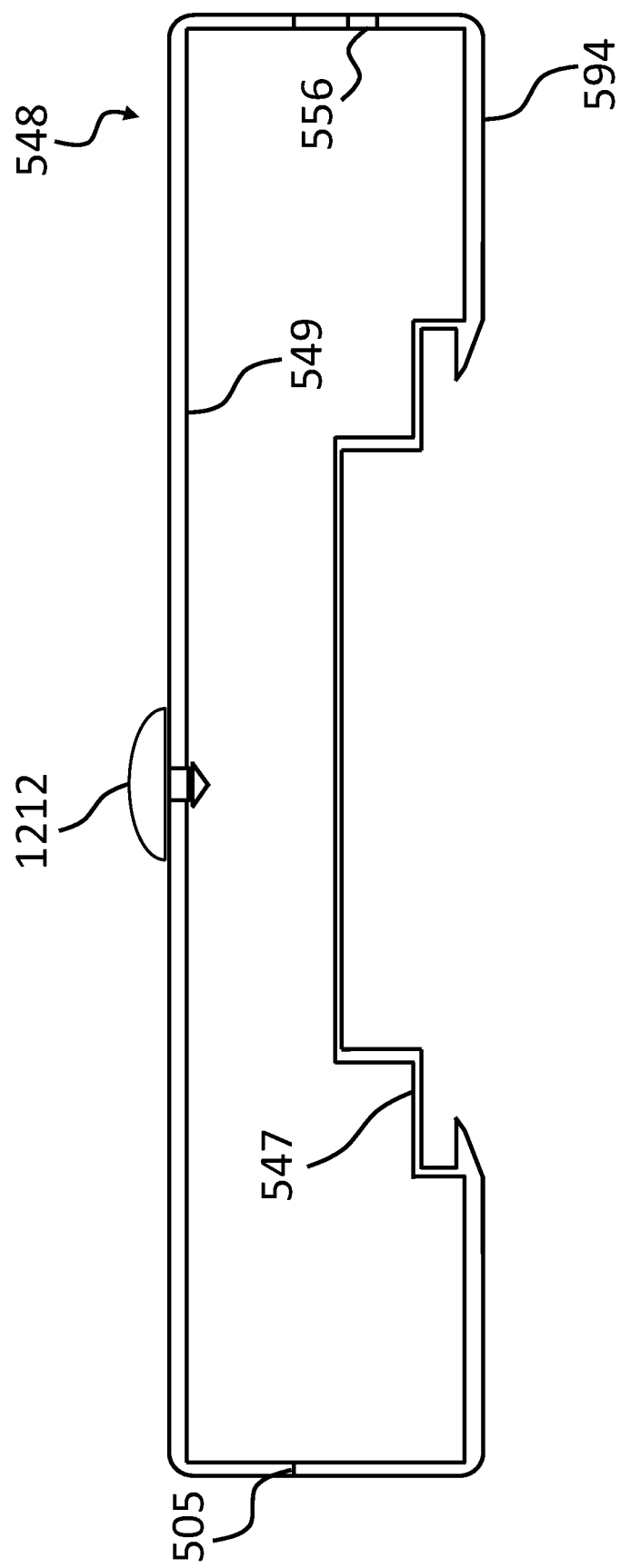
FIG. 13 is a schematic diagram of a cross-section of a portion of an exemplary external component according to an exemplary embodiment.

That said, FIG. 13 depicts an alternate embodiment where there is a hole completely through the top wall 549 with no deviation 1221, which hole is extended the male portion of the emblem 1212, as can be seen. In this regard, the hole provides a passage from the outside of the housing 548 to the inside of the housing from the side 546 (even though the emblem 1212 fills or otherwise covers hole). Still, it can be seen that the subcomponent 547 of housing 548 provides a complete barrier between the magnet/magnet apparatus of the respective embodiment and a side of the body piece opposite (the skin facing side, side 544). Corollary to this is that the subcomponent 547 of housing 548 provides a complete barrier between the magnet/magnet apparatus and an interior of the housing 548.

That said, with respect to the embodiments of FIGS. 4 and 11, where the housing subcomponent 549 include a monolithic component with respect to the portions thereof that extend across side 546, a side of the body piece opposite the side configured to interface with skin of the recipient is contiguously jointless. That is, there is no joint between components establishing the side of the body piece on side 546. Note that this is distinguished from a seamless configuration, where, for example, portions of housing subcomponent 549 can be welded together at locations on the side 546, these welds not being a joint. That said, some embodiments are also contiguously seamless with respect to the side of the body piece opposite the side configured to interface with skin of the recipient. Such can be achieved via the utilization of a monolithic component extending across the side 546. Such can be achieved, by way of example only and not by limitation, by an injection molding process and/or a blow molding process that results in a saucer shape component, as will be described in greater detail below. Accordingly, in an exemplary embodiment, the side 546 appears "clean" and unbroken and in some instances, uniform. By analogy, the side 546 could have the same structural visual attributes with respect to surface description as that of a car cab roof without a sunroof as compared to one with a sun roof.

Figure 14A:
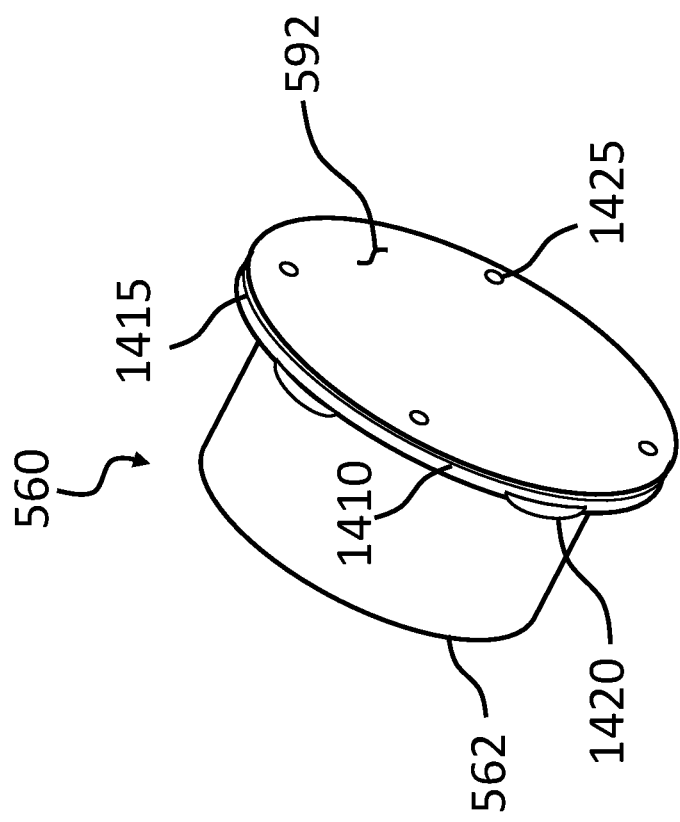
FIG. 14A is an isometric view of an exemplary magnet apparatus according to an exemplary embodiment.

The following features of some embodiments will be described with respect to FIGS. 7 and 14, where FIG. 14A depicts an isometric view of the subcomponent 560 containing the magnet 564, which is not shown, because it is eclipsed or otherwise contained entirely within housing 562.

As detailed above, some exemplary embodiments are configured such that the subcomponent 560 is configured to removably lock on to subcomponent 550 or otherwise into subcomponent 550. In an exemplary embodiment, the body piece is configured such that the magnet is turned locked to the body piece. In an exemplary embodiment, the configuration is such that a quarter turn system is utilized, although some alternate embodiments can utilize other types of turns, such as by way of example, and eighth turn, or a one third turn, or a 5/16 turn, or even a half turn or more. Any arrangement that is related to turning the subcomponent 560 by an amount less than 360° that locks the subcomponent 560 to the subcomponent 560 is encompassed within the phrase "turn lock." That said, any locking arrangement that will enable the teachings detailed herein or variations thereof to be practiced can be utilized in at least some exemplary embodiments.

That said, embodiments will be described in terms of a quarter turn system. As detailed above with respect to FIG. 5, an exemplary embodiment is such that the subcomponent 560 is configured to be moved upwards towards the subcomponent 550 in the direction of arrow 597. In an exemplary embodiment, this can be done or otherwise is done until the subcomponent 560 is seated or otherwise aligned as shown in FIG. 4, or more specifically, this is done until the surface 592 is aligned with surface 594, or otherwise such that the surface 592 is positioned relative to surface 594 in a manner having utilitarian value whether that be recessed or proud as the case may be. After this, the rotational torque is imparted on to the subcomponent 560 and/or the subcomponent 550 so as to turn the two components relative to one another (represented by arrow 598). With the embodiment associated with a quarter turn, the subcomponent 560 is turned about 90° (which includes 90°) so as to lock the subcomponent 560 in place, thus turn locking at the subcomponent 560, and thus the magnet, to the headpiece. To remove the subcomponent 560 from the subcomponent 550, and thus to remove the subcomponent 560 from the headpiece, the subcomponent is turned in the opposite direction by about 90°, and then the subcomponent 560 is moved in the direction of arrow 597 away from subcomponent 550. (It is noted that this exemplary embodiment has been described in terms of moving the subcomponent 560 relative to the subcomponent 550. It is to be understood that these results can be achieved by instead moving the subcomponent 550 relative to the subcomponent 560. It is further to be understood that these results can be achieved by instead moving both components in opposite directions relative to one another. Thus, any disclosure of movement of one subcomponent corresponds to a disclosure of moving the other subcomponent in the opposite direction and/or moving both subcomponents in opposite directions.)

Figure 5:
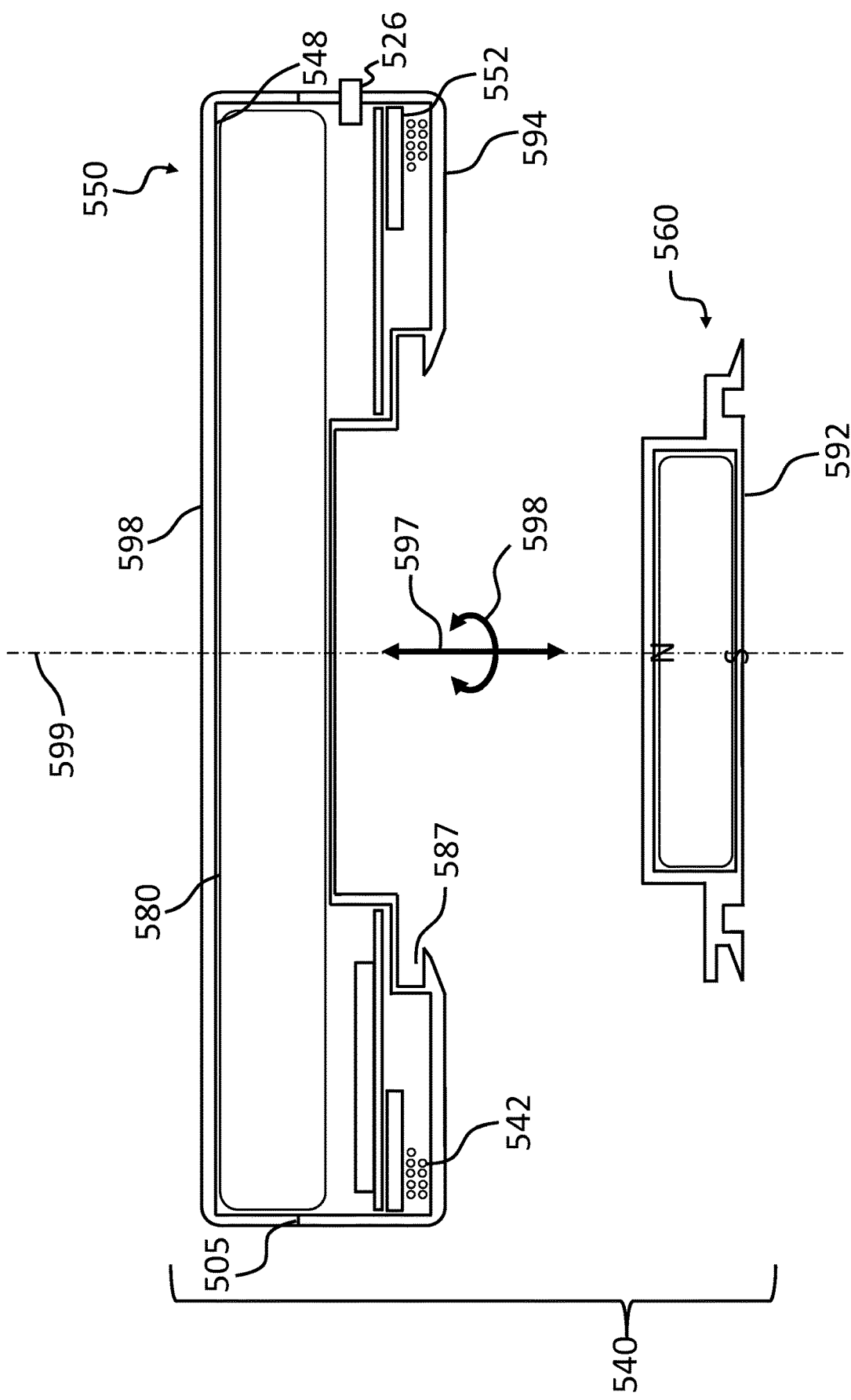
FIG. 5 is a schematic diagram of a cross-section of an exemplary external component according to the exemplary embodiment of FIG. 4, except with the components spaced apart from one another for purposes of clarity.

It is noted that the components utilized to configure the body piece to have the quarter turn lock arrangement are components that are part of the housings of the various subcomponents. In this regard, in an exemplary embodiment, the subcomponent 547 is molded or otherwise fabricated so as to have locking components as part of the housing. This is functionally represented by recess/female portion 587 as seen in FIGS. 5 in FIG. 6. Also, in this regard, in an exemplary embodiment, the housing 562 is molded so as to have flange 1410 (as labeled in FIGS. 7 and 14), which flange includes a female portion 1415 (or more than one on some other embodiments) and a plurality of male portions 1420, where FIG. 5 depicts the male portion 1420 received and the female portion 587, thus locking the subcomponent 550 to the subcomponent 560 (and vice versa).

With reference to FIG. 14A, it can be seen that the male portions 1420 are located about the perimeter of the flanged 1410 in a spaced apart manner. In an exemplary embodiment, male portions 1420 are spaced apart in an equally distant manner about the perimeter of the flange 1410. In an exemplary embodiment, there are four male portions 1420. That said, in alternate embodiments, there are fewer than four (e.g., 1, 2, or 3) and in other alternate embodiments there are more than four (e.g., 5, 6, 7, 8). Any arrangement or any number of male portions that can enable the teachings detailed herein and/or variations thereof to be practiced can be utilized in at least some exemplary embodiments. Still further, as can be seen, female portion 1415 is present so as to receive male portions of the housing subcomponent 547 (not shown in the figures), which male portions are located in an equally distant manner about the perimeter of the receptacle of the housings from portion 457 that receives the subcomponent 560. In an exemplary embodiment, there are four male portions, although in other embodiments there are fewer portions (e.g., 1, 2, or 3) and in other embodiments there are more portions (e.g., 5, 6, 7, 8). While the embodiments detailed herein have been described is having a contiguous and single female portion with respect to the subcomponents, in alternate embodiments, the female portion can be bifurcated and/or trifurcated and/or quadfurcated, etc. and/or there can be a plurality of female portions. Any arrangement that can enable the turn locking detailed herein can be utilized in at least some exemplary embodiments.

Briefly, it is noted that the subcomponent 560 includes turnkey receptacles 1425 located at the bottom thereof. In an exemplary embodiment, these receptacles are arrayed so as to enable a key having dowel pins spaced in a manner so as to be received in the pattern arrayed by receptacles 1425 so that the key (or wrench) can impart the turning torque on to subcomponent 560 (or provide the reaction torque with respect to a scenario where the torque is applied to the subcomponent 550). While the embodiment depicted herein is presented in terms of circular holes 1425, in alternate embodiments, such can be a single Allen wrench receptacle having a hexagon cross-section and/or a Phillips head screwdriver receptacle having the cruciform cross-section and/or a straight head screwdriver receptacle. That said, in an exemplary embodiment, the receptacle is configured so as to enable the torque/counter torque to be imparted utilizing a coin, such as by way of example only and not by way of limitation, an American currency quarter coin, or an equivalent sized Eurodollar coin, an Australian or New Zealand 10 cent coin, or an equivalent sized coin from another nation's currency, etc.

FIG. 15 depicts a reproduction of some of the portions of external component 540 of FIG. 4, where some components have been removed for purposes of ease of description. With respect to FIG. 15, it can be seen that there are planes 594 and 595, which planes 594 and 595 are normal to the longitudinal axis 599 of the external component 540, which axis 594 corresponds to, in this embodiment, the axis of winding of the RF coil 542 (i.e., the level of the locking location is on the same level as the coils with respect to location along the axis 599). The planes 594 and 595 are planes that extend out of the plane on which FIG. 15 is printed. The planes 594 and 595 sandwich the coil 542 therebetween. Also seen between these planes is a male portion of the subcomponent 560 of the quarter turn locking arrangement. Thus, it can be seen that in some exemplary embodiments, the magnet is turned locked to the external component 540 in general, and the housing 548 of the external component 540 in particular, where the turn locking is at a locking location parallel to the RF coil with respect to an axis of winding of the RF coil and inside a perimeter of the coil in that at least a portion of the surfaces of the housing 548 and the housing 562 that interact with one another so as to establish the locking are between the planes 594 and 595, where plane 594 located on the topmost coil portion and plane 595 is located on the bottommost coil portion. Accordingly, in an exemplary embodiment, the retention feature or otherwise the retention structure of the subcomponent 560 relative to subcomponent 550 is located on the same level were at least proximate to the level of the RF coil. In an exemplary embodiment, the retention features/structure is/.are entirely within the diameter of the RF coil Thus, in an exemplary embodiment, there is a body piece that comprises a first housing that contains an RF coil (e.g., housing 548). The magnet apparatus is turn locked to the housing via a turn lock apparatus having surfaces that abut one another so as to hold the magnet apparatus to the first housing against a direction of gravity that are located entirely at least about parallel to the RF coil relative to a direction between the first side and the opposite side. These surfaces that abut one another are the surfaces of the male and female portions that support the magnet apparatus in the housing when the magnet apparatus is positioned with respect to the direction of gravity as that seen in FIG. 15. That is, other than the fact that these surfaces are abutting one another, the subcomponent 560 would drop down away from the subcomponent 550 (if held where the direction of gravity is downward with respect to the frame of reference of the figure—alternatively, if the subcomponent 550 was pulled away from the head of the recipient, and the subcomponent 560 was magnetically coupled to the implanted component, subcomponent 560 would remain held against the head of the recipient after subcomponent 550 was moved away). Still further, in an exemplary embodiment, it can be understood that the turn lock apparatuses are located entirely within an interior perimeter of the RF coil (i.e., the innermost diameter of the inner turn of the RF coil 542).

That said, alternate embodiments can be configured where the locking location is arranged such that the locking location is not directly within the planes, but still is about parallel with the RF coil with respect to the axis of winding of the RF coil such as can be seen with respect to FIG. 16. That said, it is noted that the embodiment of FIG. 16 is presented more for purposes of illustration. In this regard, there is utilitarian value with respect positioning the coils 542 as close as possible to the surface assembly 596. Thus, an exemplary embodiment, while not depicted in the figures, is that the coils 542 are arranged as seen in FIG. 15, but the locking location is located higher than that which is depicted in FIG. 15.

With respect to the distance of the coils 542 from surface 594, FIG. 15 depicts an exemplary dimension 152 which is a distance from a tangent plane lying on the surface 594 at the bottommost portion thereof to the plane 595 which plane is located at the lowest most portion of the coil 542. In an exemplary embodiment, this distance is about 0.5 mm or no more than about 0.5 mm. In an exemplary embodiment, this distance is about 1 mm or no more than about 1 mm. In an exemplary embodiment, dimension 152 is about or no more than about 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, or about 5.0 mm, or any value or range of values between any of these numbers in 0.01 mm increments (e.g., 0.33 mm, 1.12 mm, 0.22 mm to 3.33 mm, etc.).

It is noted that in an exemplary embodiment, some and/or all of the coils 542 are embedded in the material of the housing 548.

FIG. 15 further depicts a dimension 151, which represents the distance between the two parallel planes 595 and 594, where plane 594 is the plane located on the up most portion of the coil 542. In an exemplary embodiment, this distance is about 0.8 mm or no more than about 0.8 mm. In an exemplary embodiment, dimension 151 is about 1.8 mm or no more than about 1.8 mm. In an exemplary embodiment, the dimension 151 is about or no more than about 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, or about 5.0 mm, or any value or range of values between any of these numbers in 0.01 mm increments (e.g., 0.35 mm, 1.11 mm, 0.32 mm to 2.22 mm, etc.).

Again with reference to FIG. 14A, it can be seen that the housing 562 is a structure that entails a first cylinder portion and a first disc portion, the first cylinder portion containing the magnet, the first disc portion corresponding to the portion that establishes the flange of which the locking components are part, the first disc portion also establishing the surface 592 (thus the first disc portion forms a portion of a skin interface side of the body piece). It can be seen that the first disc portion has a greater outer diameter than the first cylinder portion.

Figure 14B:
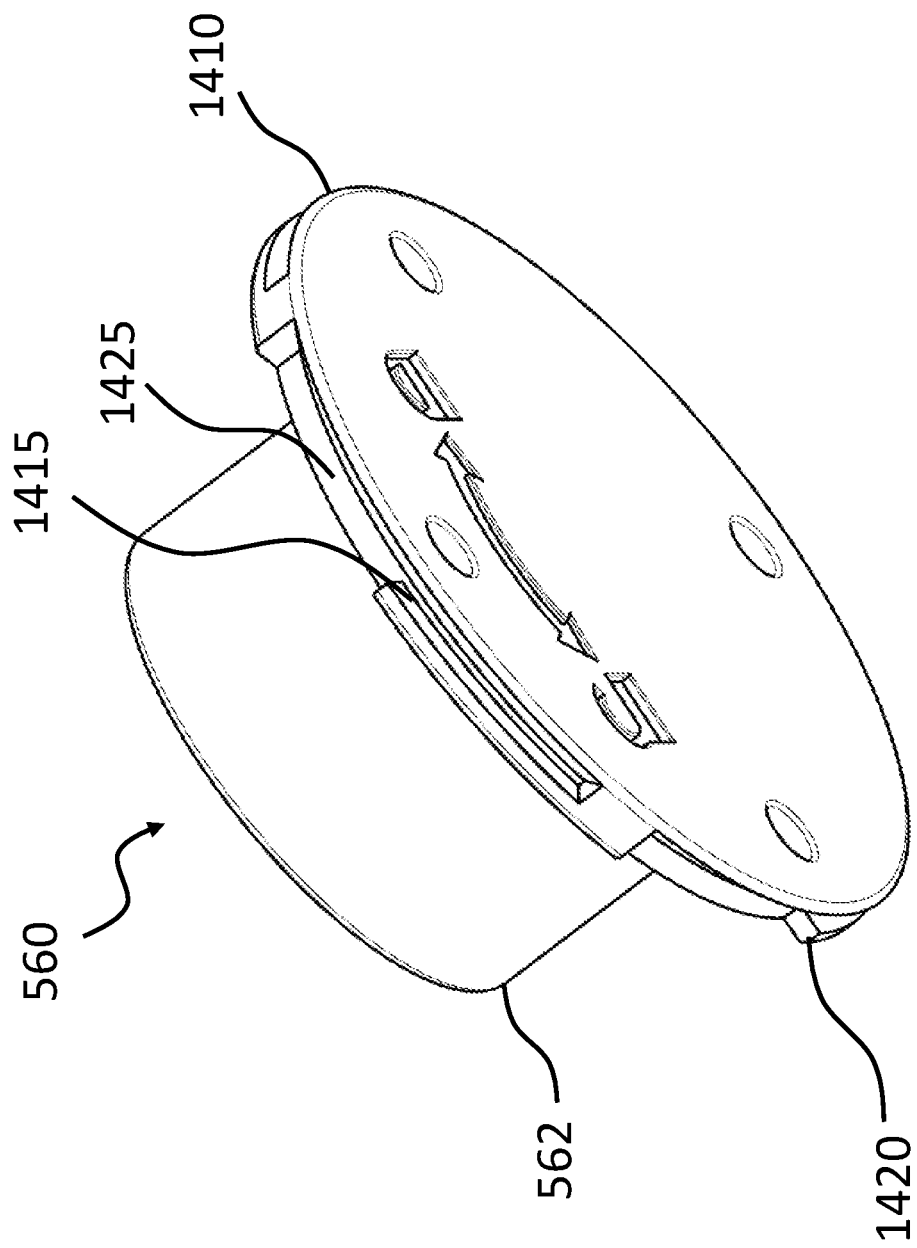
FIG. 14B is another isometric view of an exemplary magnet apparatus according to an exemplary embodiment.

FIG. 14B depicts an isometric view of an exemplary subcomponent 560. As can be seen, the subcomponent 560 includes discontinuities in the top surface of the flange, which discontinuities permit male portions of the housing 548 to be fit therethrough during the action of moving the subcomponent 560 in the direction of arrow 597. When the subcomponent 560 is rotated in the direction of arrow 598, those male portions of the housing 548 fits into the female portions 1415, thus locking the subcomponent 562 subcomponent 550, because the male portion 1420 in general, and in particular, the bottom surface thereof, rests or otherwise interfaces with the top surface of the male portion of the housing 548.

Figure 14C:
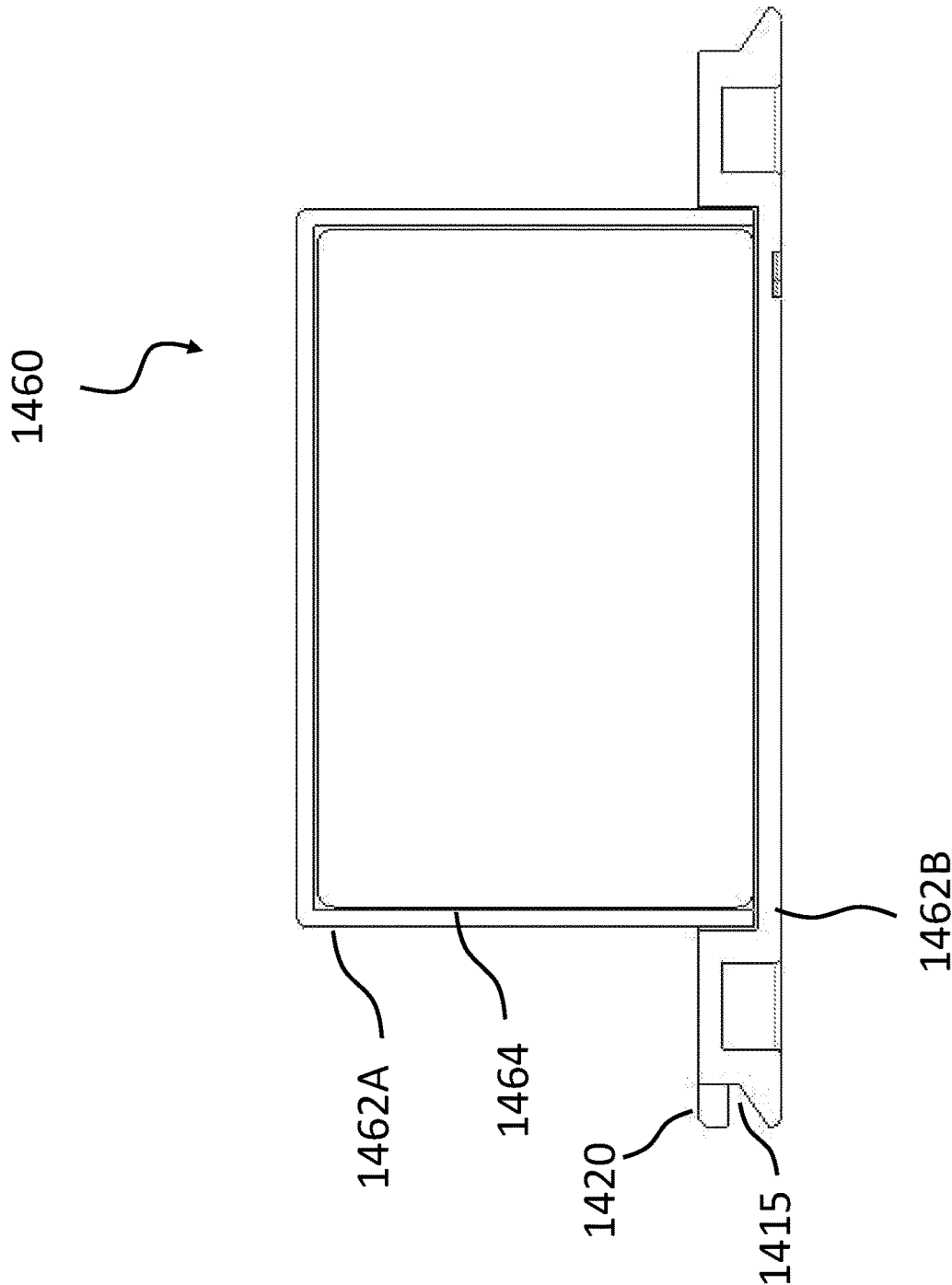
FIG. 14C is a cross-sectional view of an exemplary magnet apparatus according to an exemplary embodiment.

FIG. 14C depicts an alternate embodiment of the magnet apparatus according to an exemplary embodiment, subcomponent 1460. Subcomponent 1460 includes a magnet 1464 which is larger than magnet 564 detailed above, as can be seen. In an exemplary embodiment, the magnet 1464 is utilized to achieve a greater magnetic attraction between the external component and the implantable component. Additional details of such will be described in greater detail below. With respect to the embodiment of FIG. 14C, is noted that the subcomponent 1460 comprises a first housing sub component 1462A and a second housing subcomponent 1462B, which sub components are separate and distinct from one another. Here, the subcomponents are respectively monolithic components. In an exemplary embodiment, the subcomponent snap coupled to one another thus retaining the magnets 1464 inside the resulting housing. In an alternative embodiment, the subcomponents are welded to one another. In an exemplary embodiment, both subcomponents are made from a polymer. In some other embodiments, one of the subcomponents can be made of metal and the other a polymer, or both can be made from metal, etc. Any arrangement that can enable the teachings detailed herein and/or variations thereof to be practiced can utilize in at least some exemplary embodiments It is noted that any of the teachings detailed herein and/or variations thereof associated with the housing of the subcomponent 550 can correspond to the housing of subcomponent 1460 or 460, and visa-versa.

As noted above, there can be utilitarian value with respect to some of the embodiments detailed herein and/or variations thereof in that the magnet apparatus/subcomponent 560 cannot be seen by the viewer detailed above with respect to FIG. 8. In this regard, in an exemplary embodiment, there is an exemplary body piece configured for transcutaneous communication with an implanted component implanted in a recipient, such as by way of example only and not by way of limitation, the embodiment of FIG. 4 (external component 540). As detailed above, this exemplary body piece can include a first housing and a second housing that is a separate housing from the first housing (e.g., housing 548 and 562, respectively). In the embodiment of FIG. 4, a magnet 564 is completely enveloped by the second housing 562. Also, as can be seen from FIG. 4, the second housing forms an outer surface of the body piece (surface 592—where surface 592 in conjunction with surface 594 forms the surface assembly 596 that abuts or otherwise interfaces with the skin of the recipient when external component 540 is magnetically coupled to the recipient). In this exemplary embodiment the first housing 548 completely covers the second housing 562 with respect to views of the body piece over 180 continuous degrees of polar angle about the first housing. In this regard, FIG. 17 depicts external component 540, with a frame of reference including axis 1794, which is parallel to and lying on the plane established by surfaces 594 and 592, and also including axis 1795, which is normal to that plane and parallel to and lying on an otherwise concentric with the longitudinal axis 599 of the external component 540/the axis of rotation of the coils 542. Angle A17 is the polar angle just described. As can be seen, the polar angle A17 extends 180°. In this exemplary embodiment, the housing 562 is completely covered by the housing 548 over the 180° of the polar angle about the housing 548. Conversely, the housing 548 does not completely cover housing 562 over an angle A17 of 181 degrees or more, because once the viewer is below the plane established by the surfaces 594 and 592, the surface 592 can be seen. That said, in some alternate embodiments, where the housing 562 or otherwise the subcomponent 560 is configured such that surface 592 is recessed relative to surface 594, the angle A17 could be greater than 180° that results in the housing 548 completely covering the housing 562. Alternatively, in some alternate embodiments, where the housing 562 or otherwise the subcomponent 560 is configured such that surface 562 is proud relative to surface 594, the angle A17 would be less than 180° that results in the housing 540 a completely covering the housing 562.

Accordingly, in an exemplary embodiment, there is a body piece such as those detailed herein and/or variations thereof where the first housing completely covers the second housing with respect to views of the body piece over at least 150, 155, 160, 165, 170, 175, 180, 185, 190, 195, 200, 205, 210 degrees or more, or any value therebetween in 0.1 degree increments (e.g., over at least 155.2 degrees, 175.5 degrees, etc.).

Note that the polar angle can begin and end anywhere providing that is continuous. In this regard, it is to be understood that there are polar angles less than 180° that will always results in the housing 562 being viewed (e.g., where those angles are measured in the "southern hemisphere" as opposed to the "northern hemisphere" (i.e., the latter is above 1794)). With respect to the aforementioned embodiment, the feature of the housing 548 completely covering the housing 562 over the 180 continuous degrees is achieved by measuring the angle completely in the "northern hemisphere" (i.e., above plane 1794).

FIG. 18 depicts schematically a polar angle A18 of 170°. As can be seen, nowhere along the arc that forms the angle can the housing 562 be viewed, because housing 548 blocks the line of sight between the viewer and the housing 562.

Corollary to this is that in an exemplary embodiment, the housing 548 completely covers the housing 562 with respect to views of the body piece over 360° of azimuthal angle about the housing 548. In this regard, the azimuthal angle is the angle about longitudinal axis 599. FIG. 19 depicts this by way of schematic, where FIG. 19 is a view of the external component 540 of FIG. 4 (and FIGS. 18 and 18) looking downward from the top (i.e., looking down with respect to the frame of reference of FIG. 4/looking "down the axis 599). Axes 1999 and 1994 have been superimposed onto external component 540, where these axes are normal to each other.

The angle A19 is presented as being about 350° for purposes of understanding. As just noted, in an exemplary embodiment, the housing 548 completely covers the housing 562 with respect to views of the body piece over 360° (A19=360°) of azimuthal angle.

In view of the above, it can be seen that the azimuthal angle is measured on a plane that is normal to the plane on which the polar angle is measured. Further as can be seen, the plane on which the azimuthal angle is measured is normal to the longitudinal axis 599, and the plane on which the polar angle is measured is parallel to and lying on the longitudinal axis 599.

Figure 20:
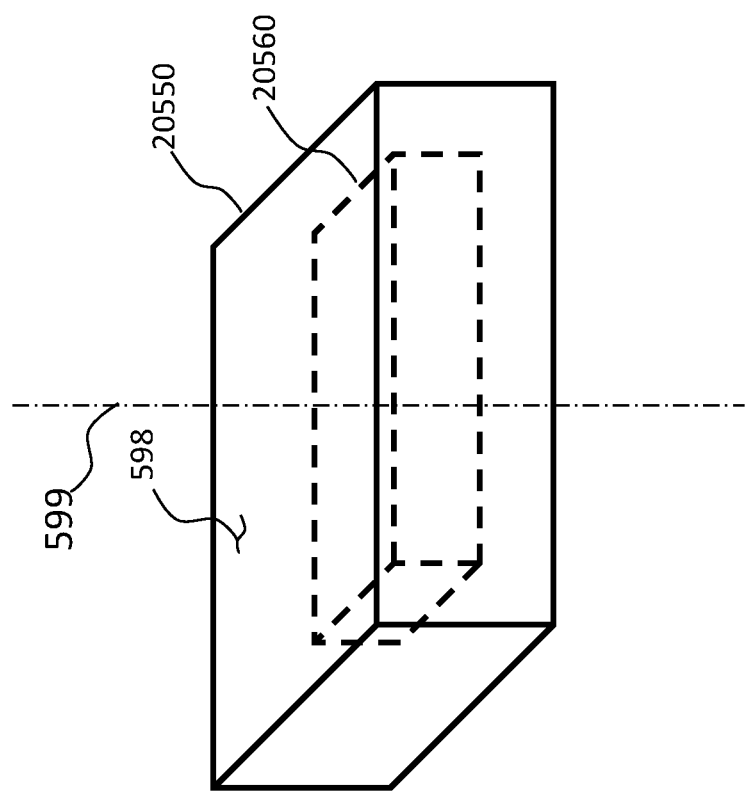
FIGS. 20 and 21 and 22 present some exemplary conceptual schematics according to an exemplary embodiment.
Figure 21:
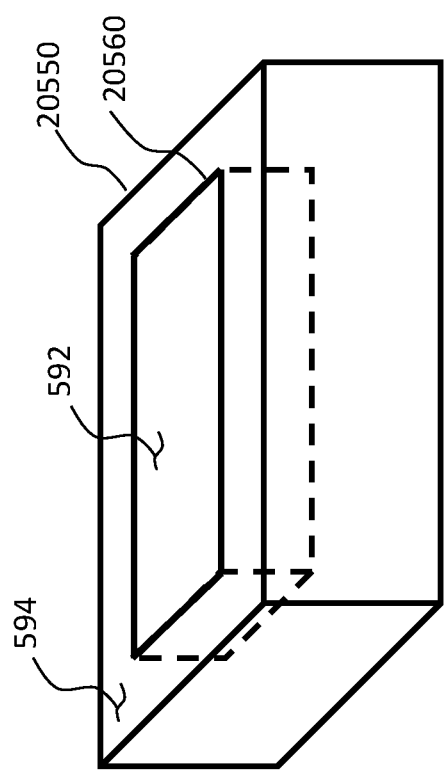
Figure 22:
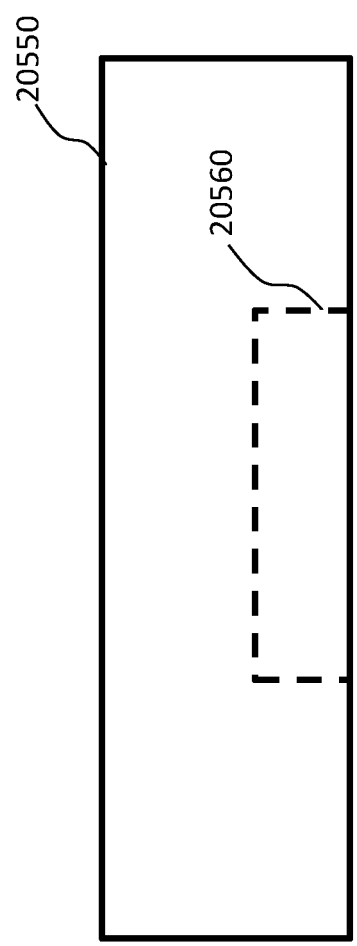

The embodiments detailed above can be described in terms of generalized rectangular cuboids. In this regard, FIG. 20 depicts a perspective view looking downwards at an angle from the top onto an exemplary generalized rectangular cuboid representing external component 540, were surface 598 is the top surface. Subcomponent 550 is represented by cuboid 20550, and subcomponent 560 is represented by cuboid 20560. FIG. 21 depicts a perspective view looking upwards an angle from the bottom on the generalized rectangular cuboid representing external component 540 of FIG. 20, where surface 592 is the bottom surface of the subcomponent 560 and surface 594 is the bottom surface of the subcomponent 550. FIG. 22 depicts a side view looking directly at the side of external component 540. The dashed lines in these figures represent elements that are "eclipsed" by structure between the viewer and the elements represented by the dashed lines. As can be seen, in terms of the generalized rectangular cuboid, the housing of subcomponent 20560 is surrounded by the housing of subcomponent 20550 at a top side and all four side sides of the cuboid.

Figure 23:
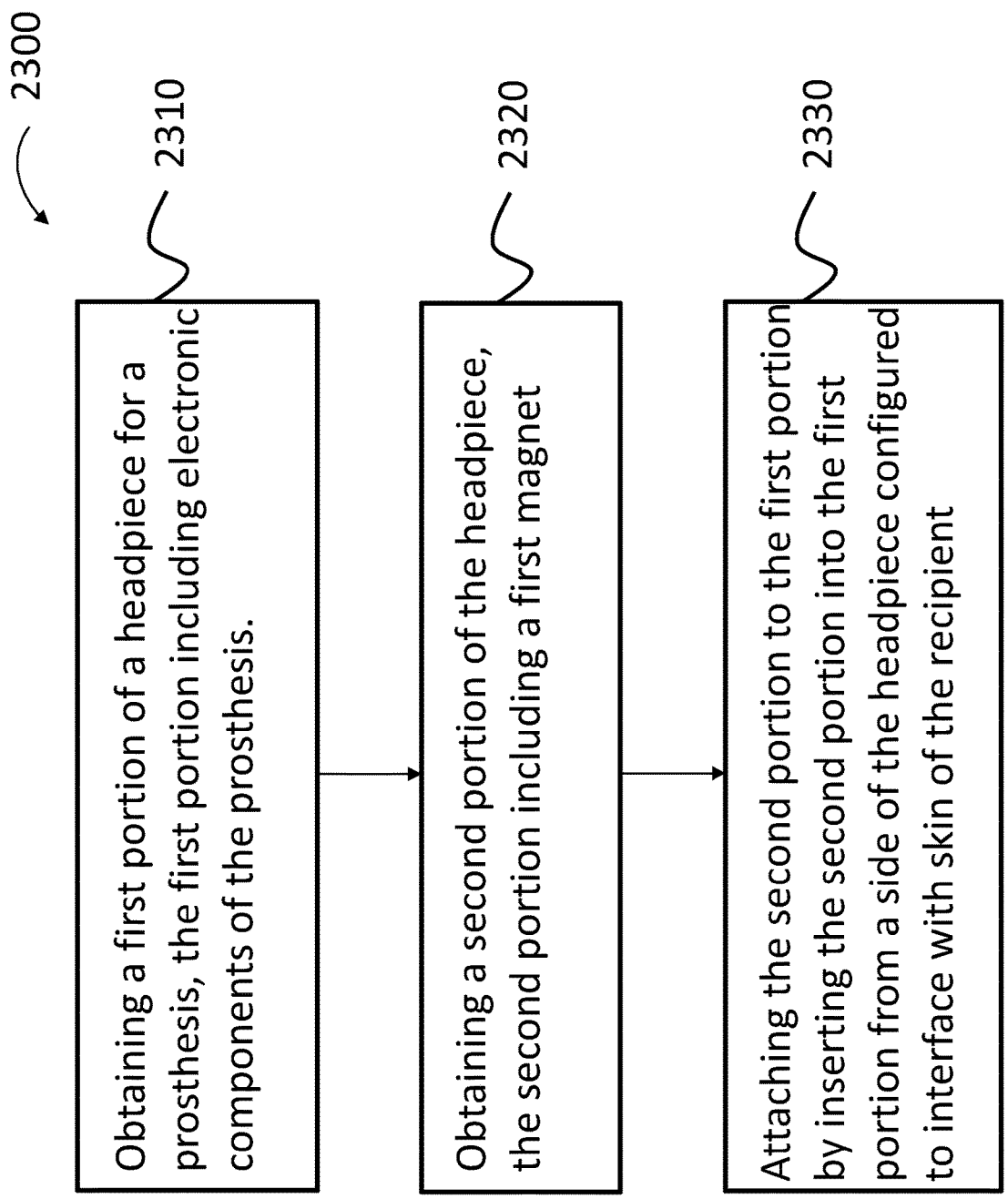
FIG. 23 presents an exemplary flowchart for an exemplary method according to an exemplary embodiment.

FIG. 23 presents a flowchart for an exemplary method 2300 according to an exemplary embodiment. Method 2300 includes method action 2310, which entails obtaining a first portion of a headpiece (i.e., the subcomponent 550 of external component 540) for a prosthesis, wherein this first portion includes electronic components of the prostheses. Method 2300 further includes method action 2320 (note that these method actions need not be practiced in the order presented in FIG. 23, and unless otherwise specified, irrespective of the order in which these methods are presented, the in which they are presented does not correspond to a limitation on the order of practice), which entails obtaining a second portion of the headpiece (i.e., the subcomponent 560 of external component 540), the second portion including a first magnet (e.g., magnet 560). Method 2300 further includes method action 2330, which entails attaching the second portion to the first portion by inserting the second portion into a receptacle of the first portion from a side of the headpiece configured to interface with skin of the recipient. In an exemplary embodiment, this entails moving the second portion into the receptacle in the first portion (the area in the bottom of housing subcomponent 547 that receives the housing 562 containing the magnet 564) in the direction of arrow 597, and then rotating the housing 562, and thus the subcomponent 560, a quarter turn (90 degrees) in the direction of arrow 598 so as to lock the housing 562/second portion to the first portion. In an exemplary embodiment, any of the attachment teachings detailed above can be utilized to practice method action 2330, and variations thereof.

Figure 24:
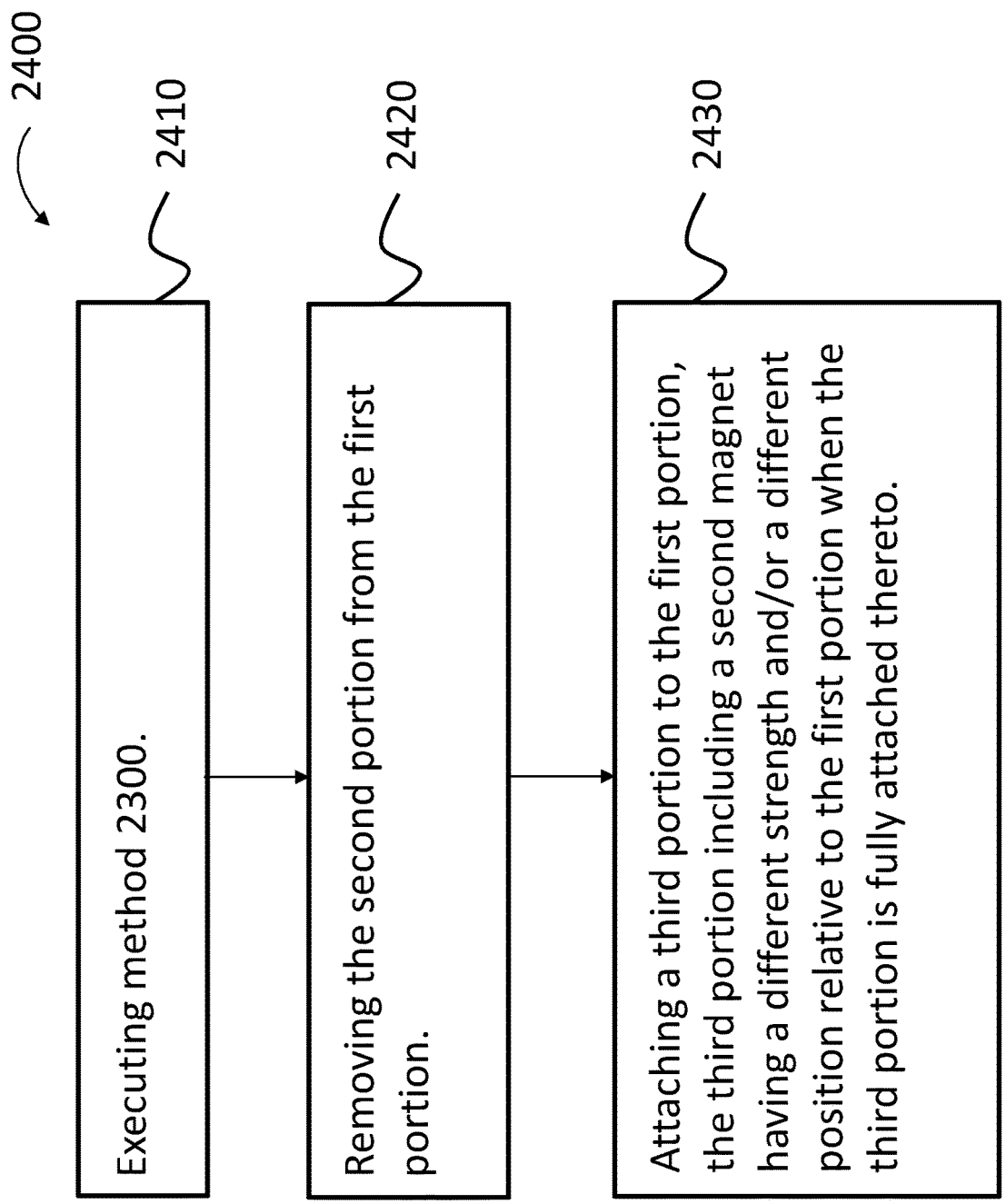
FIG. 24 presents an exemplary flowchart for an exemplary method according to an exemplary embodiment.

FIG. 24 depicts a flowchart for another exemplary method 2400 according to an exemplary embodiment. Method 2400 includes method action 2410, which entails executing method 2300. Method 2400 further includes method action 2420, which entails removing the second portion from the first portion. Method action 2420 can be executed by first rotating the housing 562, and thus the subcomponent 560 (the second portion according to this method), a quarter turn (90 degrees) in the opposite direction as that rotated during method action 2330 in the direction of arrow 598, and then moving the housing 562, and thus the subcomponent 560, away from the housing 547/receptacle therein (thus away from the first portion) in the direction of arrow 597. Method 2420 can be executed according to any of the detachment teachings detailed above according to at least some exemplary embodiments.

Method 2400 further includes method action 2430, which entails attaching a third portion to the first portion the third portion including a second magnet having a different strength and/or a different position relative to the first portion when the third portion is fully attached thereto. Method action 2430 can be executed according to method action 2330, except with the third portion instead of the second portion.

In an exemplary embodiment, method 2400 has utilitarian value with respect to changing or otherwise adjusting the resulting magnetic attraction between the external component 540 and the implanted component 450. In this regard, in at least some exemplary embodiments, the magnet or otherwise the ferromagnetic material implanted in the recipient as part of the implanted component 450 will generally not be removed in that it is implanted to be a permanent feature (i.e., not moved unless there is a failure of some implanted component warranting explanation, not moved unless there is significant obsolescence of the implanted component, not moved unless there is a significant physiological problem associated with the recipient warranting removal, etc.). Thus, the magnet or otherwise the ferromagnetic material implanted in the recipient will be a constant factor with respect to the magnetic attraction link between the external component and the implantable component. Thus, the ability to remove the magnet in the external component and replace it with a new magnet (and, thus an entirely new subcomponent 560) so as to obtain a different resulting magnetic strength between the external component and the implanted component can have utilitarian value.

That is, according to an exemplary embodiment, method 2400 results in the net attractive force being varied from that which was previously the case with the first portion. For example, by way of example only and not by way of limitation, holding all other variables constant, the magnetic flux that retains the external component 540 to the implantable component 450 can be varied such that the resulting retention force that holds the external component 540 to the skin of the recipient is different after the execution of method 2400 (greater or less—more on this below) relative to that which was the case with the permanent magnet arrangement of the second portion.

In an exemplary embodiment, method 2400 can be executed multiple times for different portions (a fourth portion, a fifth portion, a sixth portion, a seventh portion, etc.), each resulting in a different magnetic attraction force between the external component 540 and the implantable component 450. Thus, in an exemplary embodiment, there is utilitarian value with respect to executing method 2400 and variations thereof in that the resulting attraction force can be "customized," at least within a range of possible forces owing to the respective resulting attraction force resulting from a given subcomponent 560 that is utilized with the subcomponent 550. That is, in an exemplary embodiment, method 2400 can be executed so as to "test" various subcomponents 460 so as to "test" respective attraction forces to determine which one is more comfortable and/or which one provides the desired utilitarian results relative to the others.

It is noted that in an exemplary embodiment, methods 2300 and 2400 further includes the action of inserting the second portion into the first portion without moving any subportion of the first portion relative to any other subportion of the first portion. In this regard, in an exemplary embodiment, the action 2330 is executed entirely by moving the first portion and the second portion relative to one another. For example, owing to the turn lock arrangement, the external component does not include any other locking mechanism or otherwise does not require any other component to be removed and/or actuated so as to enable the attachment and/or detachment of the second portion relative to the first portion. It is further noted that in an exemplary embodiment, when the first portion is attached to the second portion, the headpiece (bodypiece) is complete, at least with respect to the methods 2300 and/or 2400 detailed herein.

Figure 25:
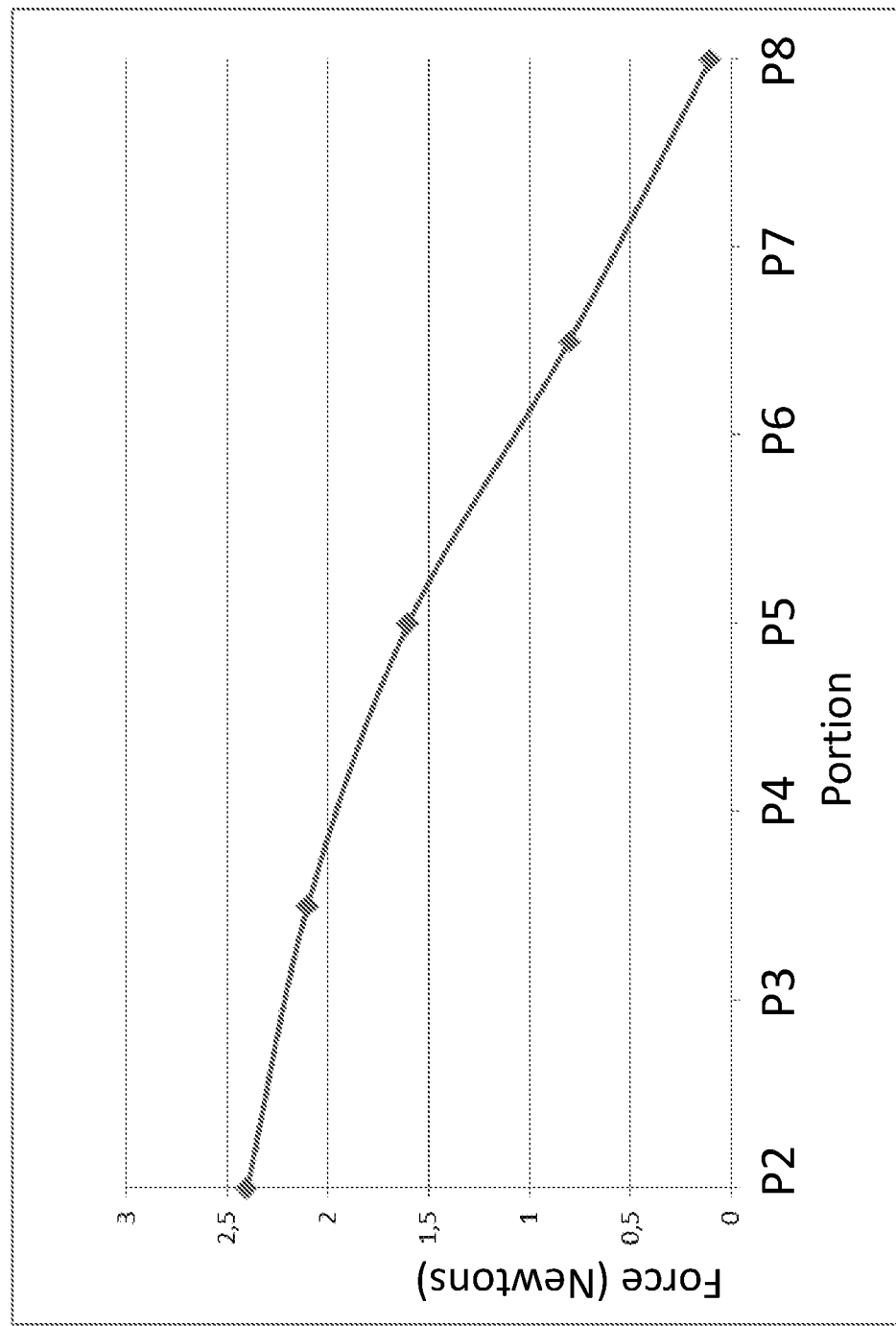
FIG. 25 is a graph presenting some exemplary data according to some exemplary embodiments.

FIG. 25 presents a chart that depicts an exemplary graph of attraction force in Newtons between the external components 540 and the implantable component 450 for various portions (P2, P3, P4, P5, P6, P7, P8) which corresponds to the top component 560 containing the magnet. As can be seen, each one results in a different attractive force for the given implant, it is noted that these results are exemplary in nature, and are based on a statistically significant sample of a given population (i.e., one having a skin thickness overlying the implantable component 450 falling within a given human factors classification, etc.).

It is noted that as a general rule, stronger magnets 564 and/or magnets positioned closer to the surface 592 would result in stronger attractive forces, all things being equal (more on this below).

To be clear, the data depicted in FIG. 25 is exemplary to illustrate a general concept for some embodiments. That said, the data is accurate for other embodiments.

As can be seen from the graph of FIG. 25, in at least some embodiments, embodiments of the teachings detailed herein can result in the attraction force between the external component 540 and the implantable component 450 being varied as a result of the substitution of the subcomponent 560 such that the attraction force can be reduced to approximately 10% of the maximum attraction force (i.e., the force resulting from the utilization of the second portion).

It is noted that while the embodiment of method 2400 has been presented in terms of removing the second portion and substituting the second portion for the third portion, in an alternative embodiment, method 2400 can be executed in terms of removing the second portion and substituting that for the fourth portion or the fifth portion or the six portion with the seventh portion with the eighth portion. Still further, it is noted that in an exemplary embodiment, method 2300 can be executed by placing another portion other than the second portion into the external component (e.g., the third portion, the fourth portion, the fifth portion, six portion, the seventh portion, the eighth portion, etc.). That is, in an exemplary embodiment, method 2400 need not necessarily start or otherwise proceed with the "strongest" resulting magnetic attraction between the external component and the implantable component, and that method 2400 can result in the substitution of the various portions so that the results of the method is that an increase in the magnetic force between the external component and the implantable component results.

Any arrangement or variation of the given methods detailed herein that can have utilitarian value can be utilized at least some exemplary embodiments.

That said, with respect to method 2400, where the second portion and the third portion are generic portions, and thus are not directly tied to the data presented on FIG. 25, in at least some embodiments, the execution of method 2400 results in the attraction force between the external component 540 and the implantable component 450 being varied relative to that which was the case at the commencement and of method 2300 such that the attraction force between the external component and the implantable component is reduced or increased by approximately 90%, 85%, 80%, 75%, 70%, 65%, 60%, 55%, 50%, 45%, 40%, 35%, 30%, 25%, 20%, 15%, 10%, 5% or less or about any value there between in about 1% increments (e.g., about 64%, about 17%, etc.). (That is, the resulting difference in changing one portion out and replacing it for another portion can be any of these values.)

Thus, in view of the above, in an exemplary embodiment, method 2400, or, more particularly, method actions 2420 and 2430 can result in the adjustment of a generated magnetic flux generated at least in part by the external component, so as to vary the resulting magnetic retention force between the external component and the implantable component, solely due to the replacement of the subcomponent 460, from a maximum retention force (all other variables held constant) to a retention force that is less than any of about 90%, 85%, 80%, 75%, 70%, 65%, 60%, 55%, 50%, 45%, 40%, 35%, 30%, 25%, 20%, 15% , 10% or about 5% of the initial force (the force resulting from the execution of method 2300), or any value there between as detailed above.

Any force can enable the teachings detailed herein to be practiced (e.g., retaining an external component of a bone conduction device to a recipient to evoke a hearing percept) can be utilized in at least some embodiments.

Figure 26:
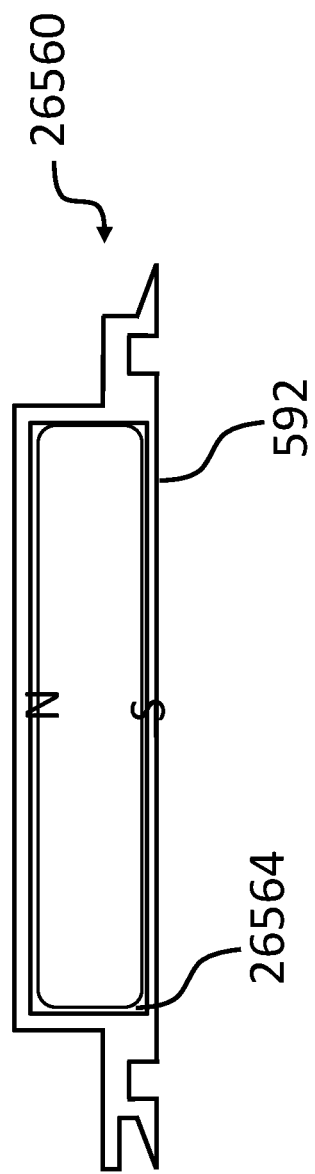
FIG. 26 is a schematic diagram of a cross-section of a portion of an exemplary external component according to an exemplary embodiment.
Figure 27:
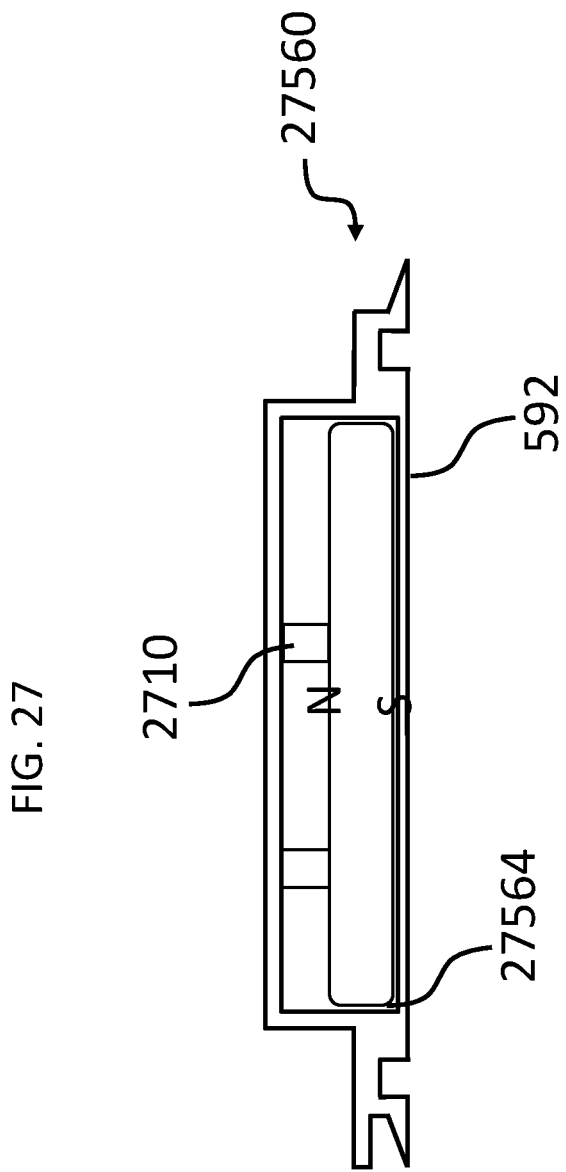
FIG. 27 is a schematic diagram of a cross-section of a portion of an exemplary external component according to an exemplary embodiment.
Figure 28:
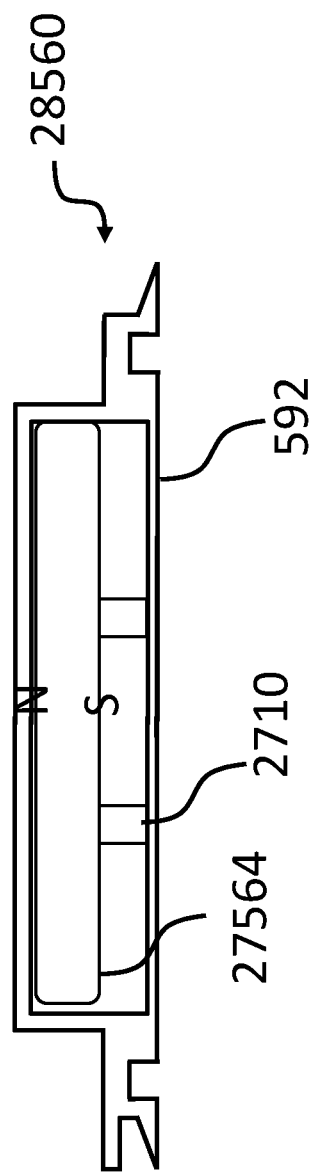
FIG. 28 is a schematic diagram of a cross-section of a portion of an exemplary external component according to an exemplary embodiment.

FIGS. 26-28 some exemplary configurations of the subcomponents containing the magnets according to some exemplary embodiments that results in a different magnetic retention force between the external component and the implantable component, all other things being equal. FIG. 26 depicts an exemplary subcomponent 26560 that includes an exemplary magnet 26564. In an exemplary embodiment, subcomponent 26560 can correspond to P2 on the graph of FIG. 25. FIG. 27 depicts an exemplary subcomponent 27650 that includes an exemplary magnet 27564, which magnet has a lower strength then the magnet 26564 of the embodiment of FIG. 26. This is depicted by way of example for illustration purposes with respect to a magnet that is "smaller" (here, less thick) than the magnet of FIG. 26. Here, for purposes of ease of manufacture, spacers 2710 have been located in the housing of the subcomponent 27560 so as to maintain the location of the magnet 27564. That said, in an alternate embodiment, the housing of the subcomponent 27560 can be thinner such that there is no space in the housing that permits the magnet to move relative to the locking portions for example. In an exemplary embodiment, this arrangement of FIG. 27 can correspond to P4 on the graph of FIG. 25.

FIG. 28 depicts yet another exemplary subcomponent 28560 that includes the magnet 27564 utilized in the embodiment of FIG. 27, except that the magnet is positioned a greater distance from surface 562 than that which is the case in the embodiment of FIG. 27. Here, spacers 2710 are utilized to keep the magnet further away from surface 562 than that which was the case in the embodiment of FIG. 27. Because the resulting distance between the magnet 27564 and the magnet implanted in the implantable component (or otherwise the ferromagnetic material implanted in the implantable component) is greater embodiments utilizing sub component 28560 relative to that which was the case in utilizing the embodiment of FIG. 27, the resulting magnetic attraction force is lower relative to that which is the case with the embodiment of FIG. 27, all other things being equal. In an exemplary embodiment, the subcomponent 28560 can correspond to P6 on the graph of FIG. 25.

It is further noted that alternate embodiments can utilize different regimes or arrangements to obtain a different magnetic force for a given subcomponent. For example, a second magnet can be included in the housing, which magnet is arranged with polarities that are opposite to the magnet 27564, so as to lessen the resulting magnetic force. Alternatively and/or in addition to this, magnets with polarities that are lined can be added so as to increase the magnetic force. Any arrangement that can be utilized to vary the resulting magnetic force that results from one subcomponent to the other subcomponent can be utilized in at least some exemplary embodiments.

In an exemplary embodiment, the various portions corresponding to the various subcomponents 560 have a distinct appearance relative to one another. In an exemplary embodiment, the various portions that are removed and/or attached from the subcomponent 550 utilized in executing method 2400 have different color and/or a different indicia relative to one another. In this regard, in an exemplary embodiment, the third portion can have at least one of a different color or a different indicia then the second portion that is visible from the outside of the headpiece when the portions are fully attached to the first portion. By way of example only and not by way of limitation, P2 can be red, P3 can be green, P4 can be blue, P5 can be purple, P6 can be black, P7 can be white, and P8 can be orange (for example, the surface 592, or at least a portion thereof, can be these colors). Still further, in an exemplary embodiment, P2 can be marked with the indicia "1," P3 can be marked with the indicia "2," P4 can be marked with the indicia "3," etc. (for example, the surface 592 can have these indicia printed thereon). That said, in an alternate embodiment, the various portions can have the same color and/or the same indicia. Still, in embodiments where the various subcomponents 560 are identifiably visibly different from one another, especially from the outside of the external component when the subcomponent 560 is fully attached to the subcomponent 550 (i.e., completely inserted and turn locked thereto), such can have utilitarian value with respect to being able to differentiate or otherwise relatively quickly determine the general magnetic force that results from the utilization of a given subcomponent 560. Such can have utilitarian value with respect to an audiologist or other healthcare professional, or even the recipient determining or otherwise experimenting with various subcomponents 560 to determine the magnetic attraction that has utilitarian value for that recipient. Alternatively and/or in addition to this, such can have utilitarian value with respect to adjusting the magnetic strength of the attraction force between the external component and the implantable component depending on the given scenario of use. For example, when the recipient is going jogging or the like, thus experiencing impact G forces that are higher than when the recipient is not jogging (working at his or her desk), a subcomponent 560 that results in a stronger magnetic force can be utilized. Thus, in an exemplary embodiment, method 2400 is executed when the recipient anticipates that a stronger force will be needed or otherwise utilitarian to hold the external component in place because the recipient will engage in an activity that results in greater G forces than that which was the case during previous scenarios of use. Still further, in an exemplary embodiment, method 2400 is executed when the recipient anticipates that a weaker force will be needed or otherwise utilitarian to hold the external component in place because the recipient will engage in an activity that results in minimal G additional forces beyond that which results in the general pull of gravity, relative to that which was the case during a previous scenario of use.

It is noted that at least some exemplary embodiments can have utilitarian value with respect to an embodiment where the body piece is a headpiece (e.g., it will not be covered by clothing and will be relatively readily viewed by a viewer), in that the magnet apparatus (e.g., the portion corresponding to subcomponent 560) in general, and the housing containing the magnet in particular, has a distinctly different appearance than the housing in which the RF coil is located (the housing 548, for example). By "distinctly different appearance," it is meant that the appearance of the magnet apparatus is such that, when the magnet apparatus is fully attached to the housing 548, the viewer will readily see that the components are two different components owing to a clear discontinuity between the appearance thereof. For example, the color of the housing in general, or the color of the under surface of the housing in particular (surface 594), could be black, and the color of the magnet apparatus/housing containing the magnet, with the color of the surface that is exposed when the magnet apparatus is fully attached to the housing 548 (surface 592) is white, or red, or green, etc. That is, the magnet apparatus is such that the person of ordinary skill in the art would recognize that it was more likely than not that the appearance thereof was purposely meant to be different than that of the housing 548. This as opposed to, for example, an embodiment where all surfaces 592 and 594 are the same color. Another example of a distinctly different appearance could be markings on the magnet apparatus (e.g., words printed on the surface 592 such as "Rotate To Remove" or "Magnet Apparatus," etc.). Again, this is entirely based on the understanding of the person of ordinary skill in the art. All of this is as opposed to an embodiment where the magnet apparatus is of a design where the magnet apparatus does not have a distinctly different appearance than the housing. (Of course the two components will be different, but by way of analogy, a car door will still "blend" with the fender on a typical new car—car doors are typically not a different color than the fender.)

It is noted that in some exemplary embodiments, the interiors of the housings detailed herein are fluidically isolated from an ambient environment thereof and/or from one another. With reference back to FIG. 6, it can be seen that the interior 648 of housing 548 is completely isolated from the ambient environment (i.e., the outside) thereof except for hole 566. (It is noted that in some embodiments, hole 566 is not present, and a microphone or other sound capture apparatuses located outside the housing 548 and is in wireless signal communication with the sound processor therein.) When the sound capture apparatus (e.g. microphone) is positioned therein, the hole 566 is thus sealed. Accordingly, the interior 648 becomes fluidically isolated from the ambient environment. In an exemplary embodiment, the interior 648 is hermetically sealed from the ambient environment. In an exemplary embodiment, the interior is sealed in a water resistant or a waterproof/watertight manner. Now with reference back to FIG. 7, it can be seen that the interior 760 of housing 562 is completely isolated from the ambient environment (i.e., the outside) thereof. Accordingly, the interior 760 is fluidically isolated from the ambient environment. In an exemplary embodiment, the interior 760 is hermetically sealed from the ambient environment. In an exemplary embodiment, the interior 760 is sealed in a water resistant or a waterproof/watertight manner. Indeed, as noted above, in an exemplary embodiment, the housing 562 is cast about the magnet therein. That said, it is noted that in some exemplary embodiments, the interior 760 of housing 562 is not sealed or otherwise not fluidically isolated from an ambient environment. Still, in such an embodiment where housing 562 is used in conjunction with housing 548, if housing 548 is sealed as detailed above, and interior of housing 548 can be fluidically isolated from an interior of housing 562, and visa-versa. Conversely, in an embodiment where housing 562 is sealed according to the teachings detailed herein, but housing 548 is not so sealed, housing 562 can be fluidically isolated from housing 548, and visa-versa.

Figure 29:
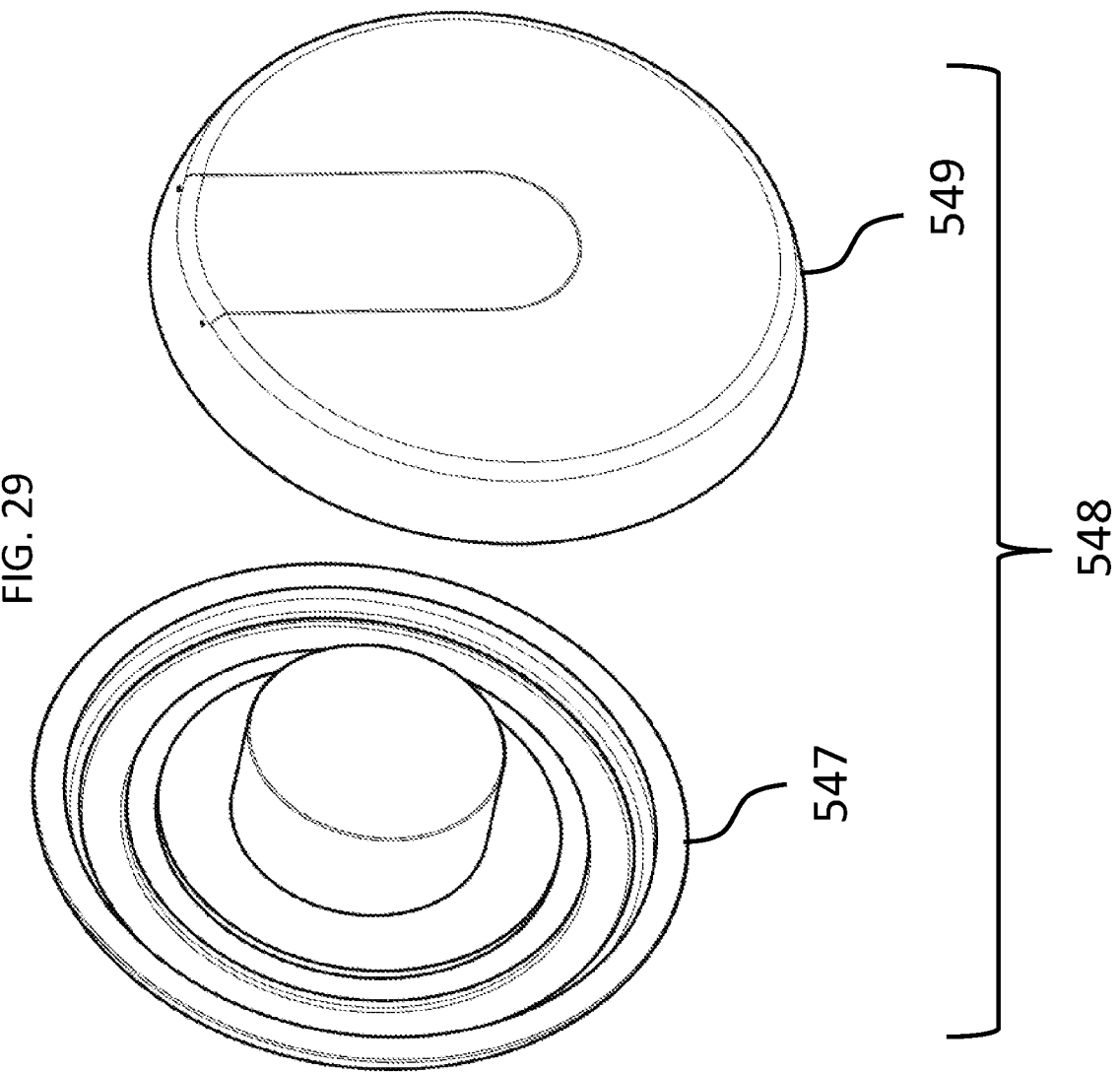
FIG. 29 is an isometric view of exemplary housing subcomponents according to an exemplary embodiment.

FIG. 29 depicts an isometric exploded view of housing 548 according to an exemplary embodiment. As can be seen, and interior isometric view of the housing subcomponent 547 is depicted, along with an exterior isometric view of the housing subcomponent 549. As can be seen, both are jointless and seamless. In an exemplary embodiment, these components are made by injection molding or blow molding or other forming techniques that have utilitarian value with respect to making the housing components detailed herein and/or variations thereof.

As noted above, in an exemplary embodiment, subcomponent 547 and 549 are polymer-based components, such as by way of example only and not by way of limitation, components that are made from hard plastic. That said, in an alternate embodiment, these components can be metallic component based components for subcomponent 549, and ceramic based component for subcomponent 547. In some alternate embodiments, all is made of metal. Any arrangement that can enable the teachings detailed herein and/or variations thereof to be practiced can be utilized in at least some exemplary embodiments.

In an exemplary embodiment, an exemplary manufacturing method entails placing the battery, the PCB, the RF coil etc. into the interior of the subcomponent 547, and then placing the subcomponent 549 over those components and otherwise attaching subcomponent 549 two subcomponent 547. In an exemplary embodiment, the subcomponents snap couple or otherwise interference fit to one another, leaving a joint at the interference location about the perimeter of those two components of the mating section. In an alternate embodiment, and/or in addition to this, the subcomponents are welded together, thus resulting in a seam at the perimeter.

Figure 30:
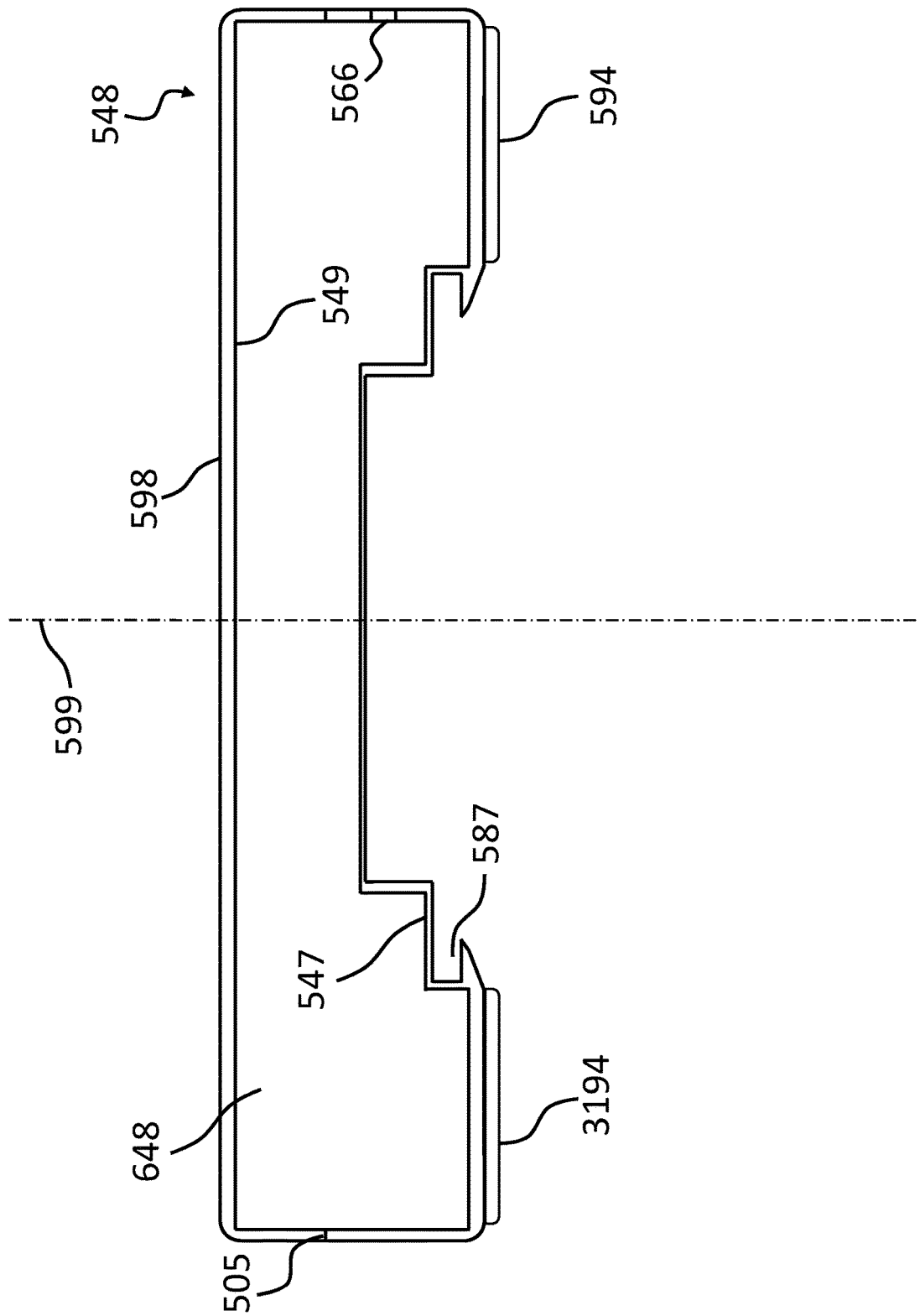
FIG. 30 is a cross-sectional view of another exemplary embodiment of a component of an external component according to an exemplary embodiment.

It is briefly noted that some embodiments can have a composite subcomponent housing arrangement. For example, with reference to FIG. 30, it can be seen that the housing 548 includes a skin interface structure 3194. In an exemplary embodiment, skin interface structure 3194 can be made of a skin friendly material. In an exemplary embodiment, this can be made of PEEK. In an exemplary embodiment, skin interface structure 3194 provides a barrier between the skin and the housing structure 548. In an exemplary embodiment, such as where the housing 548 is made of titanium, the skin interface structure 3194 can act as a thermal barrier between the structure 548 and the skin (e.g., so that the recipient does not feel a sensation of cold metal against the skin). In a similar vein, such a skin interface structure 3194 can also be placed on the bottom of the housing 562 for subcomponent 560.

Figure 31:
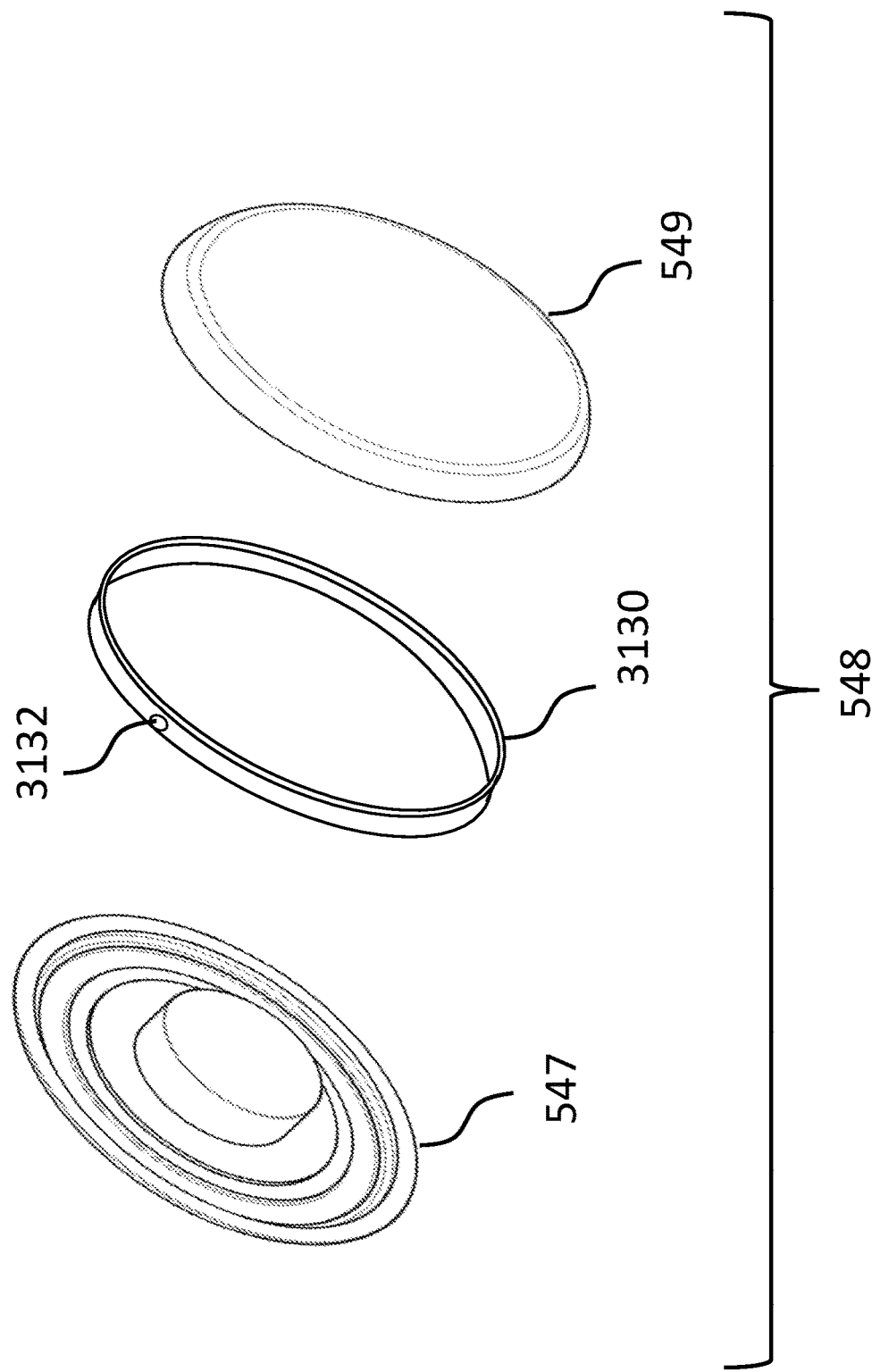
FIG. 31 is an isometric view of exemplary housing subcomponents according to another exemplary embodiment.

FIG. 31 depicts yet another exemplary alternate embodiment of the housing 548. Here, in addition to the subcomponents 547 and 549, a subcomponent 3130 is also provided. In this exemplary embodiment, subcomponent 3130 servers interface between subcomponents 547 and 549. As can be seen, subcomponent 3130 includes a hole 3132 for a sound capture apparatus, although in other embodiments, there is no such hole on the outside of subcomponent 3130. Still further, in an exemplary embodiment, subcomponent 3130 can be a component that supports or otherwise is attached to the PCB. In an exemplary embodiment, all components inside the housing 548 can be mounted to 3130 in a manner that establishes 3130 as a chassis or the like, where subcomponents 547 and 549 correspond to a body of the external component.

In an exemplary embodiment, there is a body piece configured for transcutaneous communication with an implanted component implanted in a recipient, comprising:
a first housing
a magnet; and
a second housing, wherein
the second housing completely envelops the magnet,
the second housing forms an outer surface of the body piece, and
at least one of:
the first housing completely covers the second housing with respect views of the body piece over 360 degrees of azimuthal angle and at least 170 continuous degrees of polar angle about of the first housing; or
the body piece is configured such that the second housing installable into a receptacle established by the first housing at a skin interface side of the body piece, wherein, the second housing is a structure having a first cylinder portion and a first disk portion, the first disk portion having a greater outer diameter than the first cylinder portion, the first disk portion forming a portion of a skin interfacing side of the body piece, the second housing is a structure having a first cylinder portion and a first disk portion, the first disk portion having a greater outer diameter than the first cylinder portion, the first disk portion forming a portion of a skin interfacing side of the body piece, the first disk portion includes a turn lock apparatus that interfaces with a turn lock apparatus of the first housing; the first housing includes an RF coil that extends about the first disk; and the turn lock apparatuses are located at about the same height of the body piece as the RF coil, and the turn lock apparatuses are located entirely within an interior perimeter of the RF coil.

It is noted that any disclosure of a device and/or system herein corresponds to a disclosure of a method of utilizing such device and/or system. It is further noted that any disclosure of a device and/or system herein corresponds to a disclosure of a method of manufacturing such device and/or system. It is further noted that any disclosure of a method action detailed herein corresponds to a disclosure of a device and/or system for executing that method action/a device and/or system having such functionality corresponding to the method action. It is also noted that any disclosure of a functionality of a device herein corresponds to a method including a method action corresponding to such functionality. Also, any disclosure of any manufacturing methods detailed herein corresponds to a disclosure of a device and/or system resulting from such manufacturing methods and/or a disclosure of a method of utilizing the resulting device and/or system.

Unless otherwise specified or otherwise not enabled by the art, any one or more teachings detailed herein with respect to one embodiment can be combined with one or more teachings of any other teaching detailed herein with respect to other embodiments.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A button sound processor, comprising:
an RF coil;
a sound processing apparatus; and
a magnet contained in a magnet housing apparatus, wherein
the button sound processor has a skin interface side configured to interface with skin of a recipient, and
the button sound processor is configured such that the magnet housing apparatus is not visible from a side of the button sound processor opposite the skin interface side.

2. The button sound processor of claim 1, wherein:
the button sound processor includes a battery positioned between the magnet and the side of the button sound processor opposite the side configured to interface with skin.

3. The button sound processor of claim 1, wherein:
the button sound processor comprises a first housing, the first housing containing the RF coil, the sound processor apparatus, and a battery, wherein the magnet housing apparatus is external to the first housing.

4. A body piece configured for transcutaneous communication with a component implanted in a recipient, comprising:
an RF coil; and
a magnet apparatus, wherein
the RF coil is located on a first side of the body piece relative to an opposite side of the body piece, and
the body piece is configured such that the magnet apparatus is removable out of the body piece from the first side.

5. The body piece of claim 4, wherein:
the body piece is a head piece for a hearing prosthesis.

6. The body piece of claim 4, wherein:
the body piece comprises a first housing containing the RF coil; and
the first housing presents a complete barrier between the magnet apparatus and a side of the body piece opposite the first side.

7. A body piece configured for transcutaneous communication with an implanted component implanted in a recipient, comprising:
a first housing;
a magnet; and
a second housing, wherein
the second housing completely envelops the magnet,
the second housing forms an outer surface of the body piece, and
at least one of:
the first housing completely covers the second housing with respect views of the body piece over 360 degrees of azimuthal angle and at least 100 continuous degrees of polar angle about of the first housing; or
the body piece is configured such that the second housing installable into a receptacle established by the first housing at a skin interface side of the body piece.

8. The body piece of claim 7, wherein:
the first housing completely covers the second housing with respect views of the body piece over 360 degrees of azimuthal angle and at least 100 continuous degrees of polar angle about of the first housing.

9. The body piece of claim 7, wherein:
the body piece is configured such that the second housing is installable into the receptacle established by the first housing at a skin interface side of the body piece.

10. The body piece of claim 7, wherein:
the body piece is part of an assembly that includes a behind-the-ear (BTE) body that houses a sound processing apparatus; and
the body piece is in signal communication with the BTE body.

11. The body piece of claim 4, wherein:
the body piece is configured such that the magnet apparatus is rotationally lockable in place to the body piece.

12. The body piece of claim 4, wherein:
the side of the body piece opposite the first side is established entirely by the group consisting of one surface and an emblem on top of that surface.

13. The body piece of claim 4, wherein:
the side of the body piece opposite the first side is established by: (i) a surface established by a structure extending completely from one side of the body piece to the other, which surface has a hole therein, and (ii) an indicia, wherein the indicia is snap coupled to the structure via a male portion of the indicia extending into the hole.

14. The body piece of claim 4, wherein:
the side of the body piece opposite the first side is established by (i) a surface established by a structure extending completely from one side of the body piece to the other, which surface has a hole therein, the hole extending completely from an outer side of the structure to an inner side of the structure and thus providing a passage from the outer side to the inner side; and
an inside of the body piece is separated by a barrier from the hole.

15. The body piece of claim 4, wherein:
the magnet apparatus is turn locked to a housing of the body piece via a turn lock apparatus having surfaces that abut one another, so as to hold the magnet apparatus to the housing against a direction of gravity, which are located entirely at least about parallel to the RF coil relative to a direction between the first side and the opposite side.

16. The button sound processor of claim 1, wherein:
the magnet housing apparatus is turn locked to the component of which the RF coil is apart; and a locking portion of the magnet apparatus that turn locks to the component is located on a same plane as the RF coil, which plane is normal to an axis of rotation of the RF coil.

17. The button sound processor of claim 1, wherein:

the button sound processor is defined by a housing assembly, the housing assembly establishing outer boundaries of the device which are established by no more than four monolithic structures, one of which makes up part of the magnet housing apparatus.

18. The button sound processor of claim 1, wherein:

the outside of the button sound processor is defined by a housing assembly that includes components that collectively fully envelop the sound processing apparatus and the RF coil, the components that collectively fully develop the sound processing apparatus consisting of no more than monolithic structures.

19. The body piece of claim 7, wherein:

the body piece is a button sound processor.

20. The body piece of claim 4, wherein:

magnet apparatus includes a magnet housing, a magnet and a magnet positioning structure, the housing encompassing the magnet and the magnet positioning structure; and the magnet positioning structure lifts the magnet from a bottom surface of the housing, thereby setting a magnetic force to be different than that which would be the case if the positioning structure was not present; and the magnet positioning structure is a distinct component from the magnet.

* * * * *